United States Patent [19]

Burrell et al.

[11] Patent Number: 5,618,921
[45] Date of Patent: Apr. 8, 1997

[54] ANTIBODIES FOR DETECTION OF HUMAN MDM2 PROTEIN

[75] Inventors: Marilee Burrell, Cambridge; David E. Hill, Arlington, both of Mass.; Kenneth W. Kinzler; Bert Vogelstein, both of Baltimore, Md.

[73] Assignee: The Johns Hopkins University, Baltimore, Md.

[21] Appl. No.: 390,479

[22] Filed: Feb. 17, 1995

Related U.S. Application Data

[60] Division of Ser. No. 44,619, Apr. 7, 1993, Pat. No. 5,420,263, which is a continuation-in-part of Ser. No. 903,103, Jun. 23, 1992, Pat. No. 5,411,860, which is a continuation-in-part of Ser. No. 867,840, Apr. 7, 1992, abandoned.

[51] Int. Cl.$^6$ .......................... C07K 16/32; C07K 14/47; G01N 33/53; C12N 5/12
[52] U.S. Cl. .................. 530/387.7; 530/388.85; 530/389.7; 530/350; 435/7.1; 435/330; 435/344.1
[58] Field of Search ........................... 530/387.7, 387.9, 530/388.1, 388.8, 388.85, 389.7

[56] References Cited

PUBLICATIONS

Fakharzadeh, et al., "Tumorigenic Potential Associated with Enhanced Expression of a GEne That is Amplified in a Mouse Tumor Cell Line", *The EMBO Journal*, 10(6):1565–1569 (1991).

Hinds, et al., "Mutant p53 DNA Clones From Human Colon Carcinomas Cooperate With Ras in Transforming Primary Rat Cells: A Comparison of the Hot Spot Mutant Phenotypes", *Cell Growth & Differentiation*, 1:561–580 (1990).

Romkes, et al., "Cloning and Expression of cDNA for Multiple Members of the Human Cytochrome P450IIC Subfamily", *Biochemistry*, 30(13):3247–3255 (1991).

Momand, et al., "The MDM2 Oncogene Product Forms a Complex with the p53 Protein and Inhibits p53–Mediated Transactivation," *Cell*:69:1237–1245 (1992).

Oliner, et al., "Amplification of a Gene Encoding a p53–Associated Protein in Human Sarcomas", *Nature*, 358:80–83 (1992).

Ladanyi, et al., "MDM2 Gene Amplificatin in Metastatic Osteosarcoma", *Cancer Research*, 53:16–18 (1993).

Leach, et al., "p53 Mutation and MDMS Amplification in Human Soft Tissue Sarcomas", *Cancer Research* 53:2231–2234 (1993).

Oliner, et al., "Oncoprotein MDM2 Conceals the Activation Domain of Tumour Suppressor p53", *Nature*, 362(6423):857–860 (1993).

Cahilly, et al., "Molecular Analysis and Chromosomal Mapping of Amplified Genes Isolated from a Transformed Mouse 3T3 Cell Line", *Somatic Cell and Molecular GEnetics*, 13(3):235–244 (1987).

Bueso–Ramos, "The Human MDM–2 Oncogene is Overexpressed in Leukemias", *Blood* 82(9):2617–2623 (1993).

Roitt, Essential Immunology, Ch. 4 "The Recognition of Antigen." pp. 65–68 & 74. 1991 Blackwell Sci. Publ.

*Primary Examiner*—Marian C. Knode
*Assistant Examiner*—Nancy A. Johnson
*Attorney, Agent, or Firm*—Banner & Witcoff, Ltd.

[57] ABSTRACT

A human gene has been discovered which is genetically altered in human tumor cells. The genetic alteration is gene amplification and leads to a corresponding increase in gene products. Detecting that the gene, designated hMDM2, has become amplified or detecting increased expression of gene products is diagnostic of tumorigenesis. Human MDM2 protein binds to human p53 and allows the cell to escape from p53–regulated growth. Antibodies to the human MDM2 protein and kits containing MDM2 specific antibodies are disclosed.

15 Claims, 17 Drawing Sheets

FIG. 1A-1

```
  1    GCACCGCGCGAGCTTGGCTGCTTCTGGGGC

*  AG
 84    GGCCGCGACCCCTCTGACCGAGATCCTGCTG

CGT  GC   GG  CTCCGCGCTCCCCG GAAG
168    GTGCCCTGGCCCGGAGAGTGGAATGATCCCC

ACC  GACACCCTGGGGGACC     TCG AT
252    GGAGTCTTGAGGGACCCCGACTCCAAGCGC
  1

T     C   G        C    G
336    CCTACTGATGGTGCTGTAACCACCTCACAGA
  9    P  T  D  G  A  V  T  T  S  Q
       S     E        A     S

G       C    A  G      C
420    TTATTAAAGTCTGTTGGTGCACAAAAAGACA
 37    L  L  K  S  V  G  A  Q  K  D
                                    N

A G        C           G  G  C
504    CGATTATATGATGAGAAGCAACAACATATTG
 65    R  L  Y  D  E  K  Q  Q  H  I

G                     G  A
588    GTGAAAGAGCACAGGAAAATATATACCATGA
 93    V  K  E  H  R  K  I  Y  T  M
                                     A

GC        G    AC    G  C
672    TCTGTGAGTGAGAACAGGTGTCACCTTGAAG
121    S  V  S  E  N  R  C  H  L  E
          L           S   R  Q  P
```

FIG. 1A-2

```
CTGTGTGGCCCTGTGTGTCGGAAAGATGGAGCAAGA

AGCCGC GC TTCTC TCG TCGAGCT TG ACGAC
CTTTCGCAGCCAGGAGCACCGTCCCTCCCCGGATTA

GTCGGAA ATGCGC G AAGTAG    CC    T CT
GAGGCCCAGGGCGTCGTGCTTCCGCAGTAGTCAGTC

ACCGCG TTCTCCT C GCCTC        C
GAAAACCCCGGATGGTGAGGAGCAGGCAAATGTGCA
                                 M  C

T
TTCCAGCTTCGGAACAAGAGACCCTGGTTAGACCAA
 I  P  A  S  E  Q  E  T  L  V  R  P

C          A  A  A       A
CTTATACTATGAAAGAGGTTCTTTTTTATCTTGGCC
 T  Y  T  M  K  E  V  L  F  Y  L  G
                   I  I           I

G                   C         G
TATATTGTTCAAATGATCTTCTAGGAGATTTGTTTG
 V  Y  C  S  N  D  L  L  G  D  L  F
                                  V

A  T  A  GCT  A  G       A----
TCTACAGGAACTTGGTAGTAGTCAATCAGCAGGAAT
 I  Y  R  N  L  V  V  V  N  Q  Q  E
                                  A  S  -

TG      T  C  T  G      C  CA
GTGGGAGTGATCAAAAGGACCTTGTACAAGAGCTTC
 G  G  S  D  Q  K  D  L  V  Q  E  L
             L        P  L     A  P
```

FIG. 1A-3

```
                AGCCGAGCCCGAGGGGC      83        Human  nt

CATG    CGCTCA  G    C                      Mouse  nt
     GTGCGTACGAGCGCCCA              167          Human  nt GGGCGAGC  GAGACC                            Mouse  nt
     CCCGTGAAGGAAACTGG              251          Human  nt G                  Mouse  nt
     ATACCAACATGTCTGTA              335          Human  nt
      N    T    N    M    S    V      8          Human  a.a.
                                                 Mouse  a.a.

A                                      Mouse  nt
     AGCCATTGCTTTTGAAG              419          Human  nt
      K    P    L    L    L    K     36          Human  a.a.
                                                 Mouse  a.a.

G                  Mouse  nt
     AGTATATTATGACTAAA              503          Human  nt
      Q    Y    I    M    T    K     64          Human  a.a.
                                                 Mouse  a.a.

A    C    G    T                           Mouse  nt
     GCGTGCCAAGCTTCTCT              587          Human  nt
      G    V    P    S    F    S     92          Human  a.a.
                                                 Mouse  a.a.

-----        T    C                         Mouse  nt
     CATCGGACTCAGGTACA              671          Human  nt
      S    S    D    S    G    T    120          Human  a.a.
       -    -                                    Mouse  a.a.

CA                                          Mouse  nt
     AGGAAGAGAAACCTTCA              755          Human  nt
      Q    E    E    K    P    S    148          Human  a.a.
      P                                          Mouse  a.a.
```

FIG. 1B-1

```
             TG       AA             TG
756  TCTTCACATTTGGTTTCTAGACCATCT
149    S   S   H   L   V   S   R   P   S
                   D       I           L

G   G   G   CC  G   G       G  GG
840  GGTGAACGACAAAGAAAACGCCACAAA
177    G   E   R   Q   R   K   R   H · K
                   H                   R   R

G   CAGCGGCGGCACGAGCA CAGT
924  ATATGT----------------TGTGAA
205    I   C   -   -   -   -   -   C   E
       M       S   G   G   T   S   S   S

G       T           CC
993  GTAAGTGAACATTCAGGTGATTGGTTG
228    V   S   E   H   S   G   D   W   L
                                       C

G       C       G       C
1077 TCAGAAGATTATAGCCTTAGTGAAGAA
256    S   E   D   Y   S   L   S   E   E
                                       D

A   A   C           C   T
1161 GGGGAGAGTGATACAGATTCATTTGAA
284    G   E   S   D   T   D   S   F   E

T               C       A
1245 AATCCCCCCCTTCCATCACATTGCAAC
312    N   P   P   L   P   S   H   C   N
                                       K

A
1329 GAAATCTCTGAGAAAGCCAAACTGGAA
340    E   I   S   E   K   A   K   L   E
```

FIG. 1B-2

```
                T C                             G
       ACCTCATCTAGAAGGAGAGCAATTAGTGAGACAGAAGAA
        T  S  S  R  R  R  A  I  S  E  T  E  E
                       S

------------     G             CCG         G
       TCTGATAGTATTTCCCTTTCCTTTGATGAAAGCCTGGCT
        S  D  S  I  S  L  S  F  D  E  S  L  A
        -  -  -  -                 P           G

C      C     C G C    A       C    C
       AGAAGCAGTAGCAGTGAATCTACAGGGACGCCATCGAAT
        R  S  S  S  S  E  S  T  G  T  P  S  N
        S                       E              H

T            C  G
       GATCAGGATTCAGTTTCAGATCAGTTTAGTGTAGAATTT
        D  Q  D  S  V  S  D  Q  F  S  V  E  F

G C G          G            C    GG
       GGACAAGAACTCTCAGATGAAGATGATGAGGTATATCAA
        G  Q  E  L  S  D  E  D  D  E  V  Y  Q
        H                                     R

G          G                         G T
       GAAGATCCTGAAATTTCCTTAGCTGACTATTGGAAATGC
        E  D  P  E  I  S  L  A  D  Y  W  K  C
        G

C  A          C         A  C
       AGATGTTGGGCCCTTCGTGAGAATTGGCTTCCTGAAGAT
        R  C  W  A  L  R  E  N  W  L  P  E  D
              T                             D

G T G A     A     G     G
       AACTCAACACAAGCTGAAGAGGGCTTTGATGTTCCTGAT
        N  S  T  Q  A  E  E  G  F  D  V  P  D
        A                             L
```

FIG. 1B-3

```
       CA        GC   C              Mouse nt
   AATTCAGATGAATTATCT       839      Human nt
     N  S  D  E  L  S       176      Human a.a.
        T           P                Mouse a.a.

AGC G                  Mouse nt
   CTGTGTGTAATAAGGGAG        923     Human nt
     L  C  V  I  R  E        204     Human a.a.
              E  L                   Mouse a.a.

A          C  A    C            Mouse nt
   CCGGATCTTGATGCTGGT        992     Human nt
     P  D  L  D  A  G       227      Human a.a.
     Q           D                   Mouse a.a.

G        G               Mouse nt
   GAAGTTGAATCTCTCGAC       1076     Human nt
     E  V  E  S  L  D        255     Human a.a.
                                     Mouse a.a.

.C  A  C        A               Mouse nt
   GTTACTGTGTATCAGGCA       1160     Human nt
     V  T  V  Y  Q  A        283     Human a.a.
                    T                Mouse a.a.

C                           Mouse nt
   ACTTCATGCAATGAAATG       1244     Human nt
     T  S  C  N  E  M        311     Human a.a.
                                     Mouse a.a.

G              T                Mouse nt
   AAAGGGAAAGATAAAGGG       1228     Human nt
     K  G  K  D  K  G        339     Human a.a.
                 V                   Mouse a.a.

G  C       GCTG C  A            Mouse nt
   TGTAAAAAAACTATAGTG       1412     Human nt
     C  K  K  T  I  V        367     Human a.a.
     G        L  T  E                Mouse a.a.
```

FIG. IC-1

```
              G T A     C       C         G
1413    AATGATTCCAGAGAGTCATGTGTTGAGGAA
 368      N D S R E S C V E E
              A K     P       A

C   A     G       C C           G
1494    TCTCAGCCATCAACTTCTAGTAGCATTATT
 395      S Q P S T S S S I I
                                        V

C                   C CT       G
1578    GAAGAGAGTGTGGAATCTAGTTTGCCCCTT
 423      E E S V E S S L P L
          D                 F   S

T C     G T     C C     T A
1662    GTCCATGGCAAAACAGGACATCTTATGGCC
 451      V H G K T G H L M A
                                        S

G     C                         G
1746    AGACAACCAATTCAAATGATTGTGCTAACT
 479      R Q P I Q M I V L T
                                        S

1830    TAACCCTAGGAATTTAGACAACCTGAAATT
1914    TTAGTATAATTGACCTACTTTGGTAGTGGA
1998    ACTCCTAATTTTAAATAATTTCTACTCTGT
2082    ATGTAACTTATTATTTTTTTGAGACCGAG
2166    CTCTGCCCTCCCCGGGTTCGCACCATTCTC
2250    TAATTTTTTGTACTTTTAGTAGAGACAGGG
2334    CTCGGCCTCCCAAAGTGCTGGGATTACAGG
```

FIG. IC-2

```
 G  CAGC    G   G   GGCCGA      GA GC C  TG    C
AAT---GATGATAAAATTACACAAGCTTCACAATCAC
 N  -  D   D  K  I  T  Q  A  S  Q  S
    D  S   E  E      A  E     T  P  L

AGC                    G--- A
TATAGCAGCCAAGAAGATGTGAAAGAGTTTGAAAGGG
 Y  S  S  Q  E  D  V  K  E  F  E  R
                                S          L  -  K

C      A           C  C  G   G  G
AATGCCATTGAACCTTGTGTGATTTGTCAAGGTCGAC
 N  A  I  E  P  C  V  I  C  Q  G  R

T  C  G                       A   A  C
TGCTTTACATGTGCAAAGAAGCTAAAGAAAAGGAATA
 C  F  T  C  A  K  K  L  K  K  R  N

C  AA    C           CTCA A  A   T
TATTTCCCCTAGTTGACCTG---TCTATAAGAGAATT
 Y  F  P
       N

TATTCACATATATCAAAGTGAGAAAATGCCTCAATTC
ATAGTGAATACTTACTATAATTTGACTTGAATATGTA
CTTAAATGAGAAGTACTTGGTTTTTTTTTTCTTAAAT
TCTTGCTCTGTTACCCAGGCTGGAGTGCAGTGGGTGA
CTGCCTCAGCCTCCCAATTAGCTTGGCCTACAGTCAT
TTTCACCGTGTTAGCCAGGATGGTCTCGATCTCCTGA
CATGAGCCACCG
```

FIG. 1C-3

```
         G    G         C                              Mouse nt
       AAGAAAGTGAAGACTAT            1493               Human nt
         Q    E    S    E    D    Y  394              Human a.a.
                             D                         Mouse a.a.

G         G    GC                             Mouse nt
       AAGAAACCCAAGACAAA             1577              Human nt
         E    E    T    Q    D    K  422              Human a.a.
                        H                              Mouse a.a.

C                                   Mouse nt
       CTAAAAATGGTTGCATT             1661              Human nt
         P    K    N    G    C    I  450              Human a.a.
                                                       Mouse a.a.

G    C                         Mouse nt
       AGCCCTGCCCAGTATGT             1745              Human nt
         K    P    C    P    V    C  478              Human a.a.
                                                       Mouse a.a.

T                   *                           Mouse nt
       ATATATTTCTAACTATA             1829              Human nt
                                     491              Human a.a.
                                                       Mouse a.a.

ACATAGATTTCTTCTCT             1913              Human nt
       GCTCATCCTTTACACCA             1997              Human nt
       ATGTATATGACATTTAA             2081              Human nt
       TCTTGGCTCACTGCAAG             2165              Human nt
       CTGCCACCACACCTGGC             2249              Human nt
       CCTCGTGATCCGCCCAC             2333              Human nt
                                     2372              Human nt
```

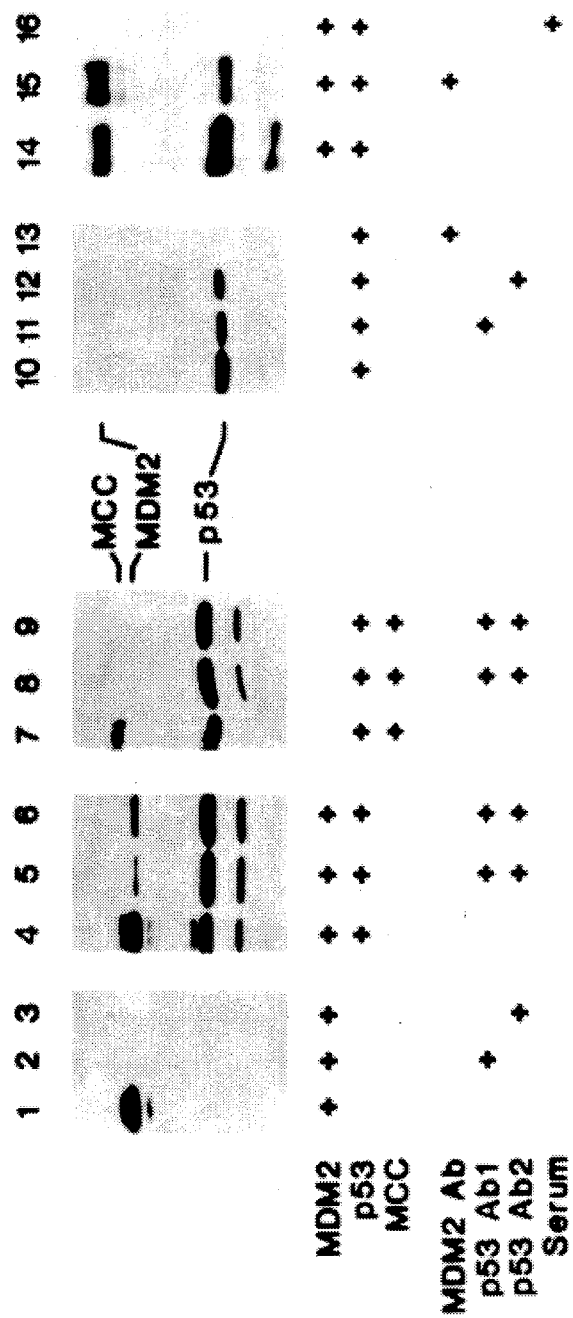

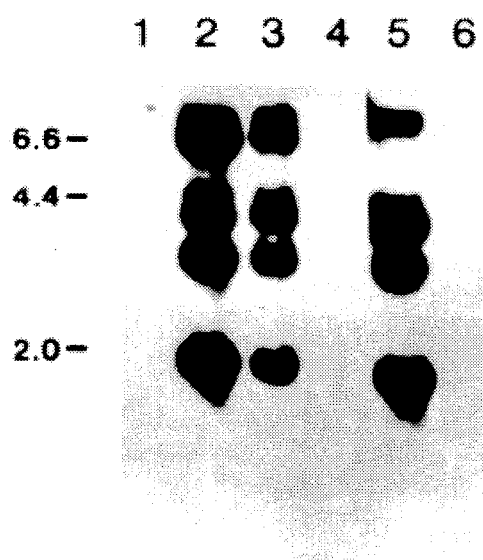 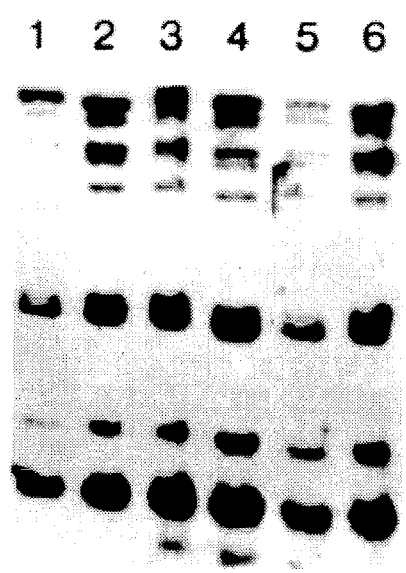
FIG. 3A MDM2
FIG. 3B DCC

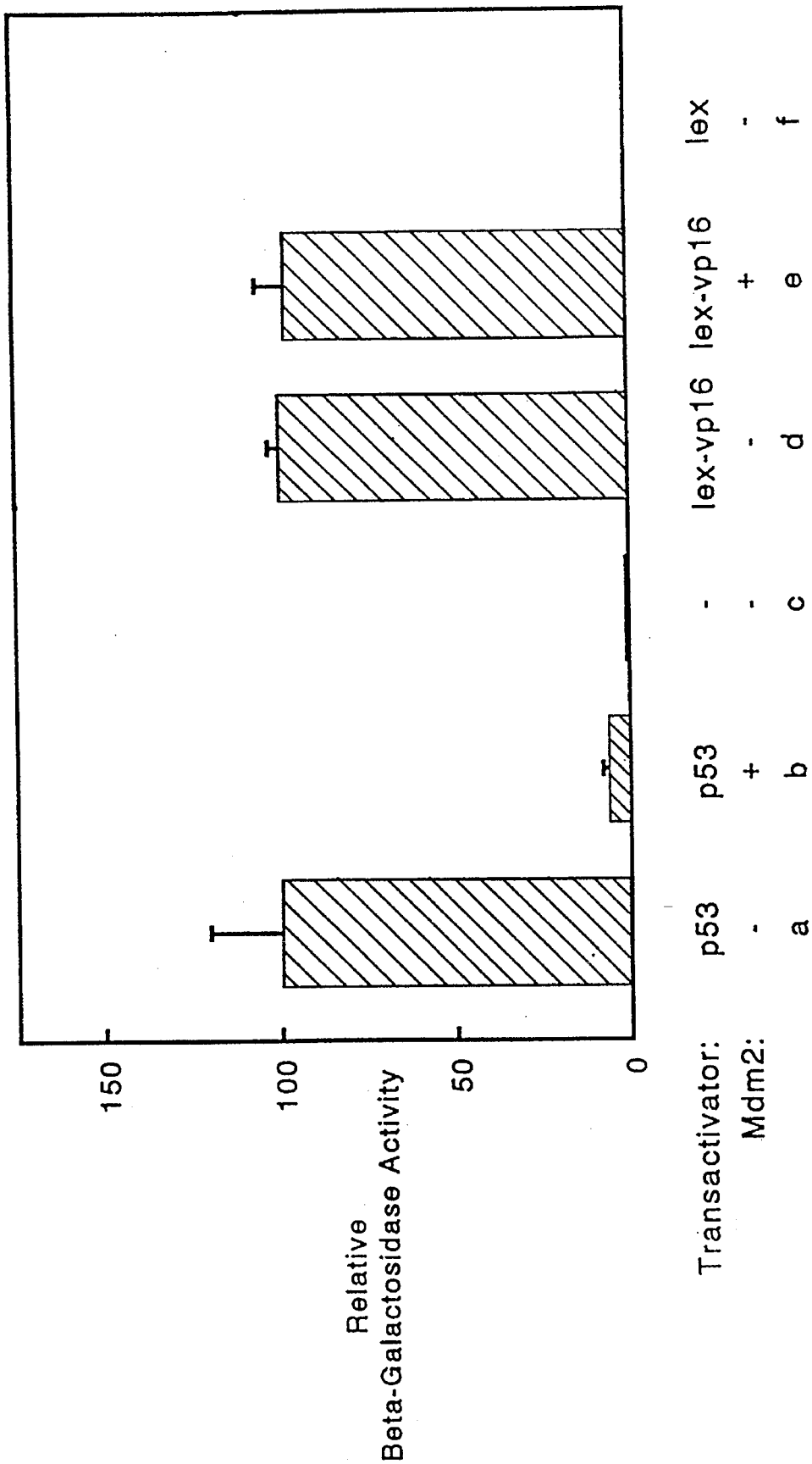

Mdm2 codons:  1-140  1-135  1-158  1-118  1-89  1-41  40-158  40-118  None

— 53

— 46

— 30 p53 codons:  13-57  1-41  13-41  19-41  13-35  None

— 112

— 30

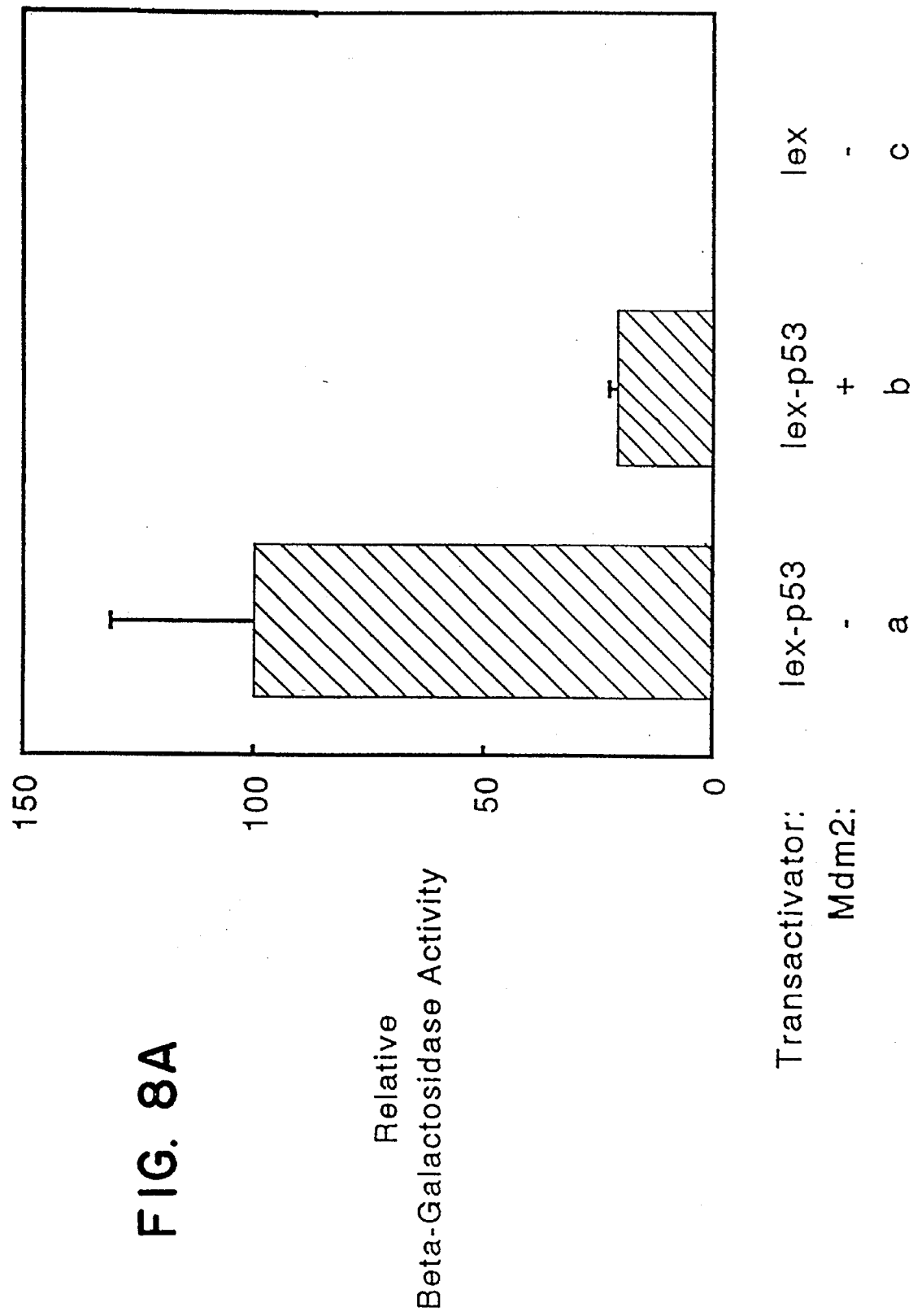

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 64 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Homo sapiens ( v i i i ) POSITION IN GENOME:
( A ) CHROMOSOME/SEGMENT: 17q ( x i ) SEQUENCE DESCRIPTION: SEQ ID NO:1:

| Met | Glu | Glu | Pro | Gln | Ser | Asp | Pro | Ser | Val | Glu | Pro | Pro | Leu | Ser | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Thr | Phe | Ser | Asp | Leu | Trp | Lys | Leu | Leu | Pro | Glu | Asn | Asn | Val | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Pro | Leu | Pro | Ser | Gln | Ala | Met | Asp | Asp | Leu | Met | Leu | Ser | Pro | Asp |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asp | Ile | Glu | Gln | Trp | Phe | Thr | Glu | Asp | Pro | Gly | Pro | Asp | Glu | Ala | Pro |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

( 2 ) INFORMATION FOR SEQ ID NO:2:

( i ) SEQUENCE CHARACTERISTICS:
( A ) LENGTH: 2372 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens
( H ) CELL LINE: CaCo-2

( v i i i ) POSITION IN GENOME:
( B ) MAP POSITION: 12q12-14

( i x ) FEATURE:
( A ) NAME/KEY: CDS
( B ) LOCATION: 312..1784

( x i ) SEQUENCE DESCRIPTION: SEQ ID NO:2:

| GCACCGCGCG | AGCTTGGCTG | CTTCTGGGGC | CTGTGTGGCC | CTGTGTGTCG | GAAAGATGGA | 60  |
| GCAAGAAGCC | GAGCCCGAGG | GGCGGCCGCG | ACCCCTCTGA | CCGAGATCCT | GCTGCTTTCG | 120 |
| CAGCCAGGAG | CACCGTCCCT | CCCCGGATTA | GTGCGTACGA | GCGCCCAGTG | CCCTGGCCCG | 180 |
| GAGAGTGGAA | TGATCCCCGA | GGCCCAGGGC | GTCGTGCTTC | CGCAGTAGTC | AGTCCCCGTG | 240 |

```
AAGGAAACTG GGGAGTCTTG AGGGACCCCC GACTCCAAGC GCGAAAACCC CGGATGGTGA                    300

GGAGCAGGCA A ATG TGC AAT ACC AAC ATG TCT GTA CCT ACT GAT GGT GCT                      350
             Met Cys Asn Thr Asn Met Ser Val Pro Thr Asp Gly Ala
              1           5                   10

GTA ACC ACC TCA CAG ATT CCA GCT TCG GAA CAA GAG ACC CTG GTT AGA                       398
Val Thr Thr Ser Gln Ile Pro Ala Ser Glu Gln Glu Thr Leu Val Arg
     15               20                   25

CCA AAG CCA TTG CTT TTG AAG TTA TTA AAG TCT GTT GGT GCA CAA AAA                       446
Pro Lys Pro Leu Leu Leu Lys Leu Leu Lys Ser Val Gly Ala Gln Lys
 30               35                   40                    45

GAC ACT TAT ACT ATG AAA GAG GTT CTT TTT TAT CTT GGC CAG TAT ATT                       494
Asp Thr Tyr Thr Met Lys Glu Val Leu Phe Tyr Leu Gly Gln Tyr Ile
             50                   55                   60

ATG ACT AAA CGA TTA TAT GAT GAG AAG CAA CAA CAT ATT GTA TAT TGT                       542
Met Thr Lys Arg Leu Tyr Asp Glu Lys Gln Gln His Ile Val Tyr Cys
         65                   70                   75

TCA AAT GAT CTT CTA GGA GAT TTG TTT GGC GTG CCA AGC TTC TCT GTG                       590
Ser Asn Asp Leu Leu Gly Asp Leu Phe Gly Val Pro Ser Phe Ser Val
     80                   85                   90

AAA GAG CAC AGG AAA ATA TAT ACC ATG ATC TAC AGG AAC TTG GTA GTA                       638
Lys Glu His Arg Lys Ile Tyr Thr Met Ile Tyr Arg Asn Leu Val Val
 95                  100                  105

GTC AAT CAG CAG GAA TCA TCG GAC TCA GGT ACA TCT GTG AGT GAG AAC                       686
Val Asn Gln Gln Glu Ser Ser Asp Ser Gly Thr Ser Val Ser Glu Asn
110              115                  120                  125

AGG TGT CAC CTT GAA GGT GGG AGT GAT CAA AAG GAC CTT GTA CAA GAG                       734
Arg Cys His Leu Glu Gly Gly Ser Asp Gln Lys Asp Leu Val Gln Glu
             130                  135                  140

CTT CAG GAA GAG AAA CCT TCA TCT TCA CAT TTG GTT TCT AGA CCA TCT                       782
Leu Gln Glu Glu Lys Pro Ser Ser Ser His Leu Val Ser Arg Pro Ser
         145                  150                  155

ACC TCA TCT AGA AGG AGA GCA ATT AGT GAG ACA GAA GAA AAT TCA GAT                       830
Thr Ser Ser Arg Arg Arg Ala Ile Ser Glu Thr Glu Glu Asn Ser Asp
     160                  165                  170

GAA TTA TCT GGT GAA CGA CAA AGA AAA CGC CAC AAA TCT GAT AGT ATT                       878
Glu Leu Ser Gly Glu Arg Gln Arg Lys Arg His Lys Ser Asp Ser Ile
175                  180                  185

TCC CTT TCC TTT GAT GAA AGC CTG GCT CTG TGT GTA ATA AGG GAG ATA                       926
Ser Leu Ser Phe Asp Glu Ser Leu Ala Leu Cys Val Ile Arg Glu Ile
190                  195                  200                  205

TGT TGT GAA AGA AGC AGT AGC AGT GAA TCT ACA GGG ACG CCA TCG AAT                       974
Cys Cys Glu Arg Ser Ser Ser Ser Glu Ser Thr Gly Thr Pro Ser Asn
             210                  215                  220

CCG GAT CTT GAT GCT GGT GTA AGT GAA CAT TCA GGT GAT TGG TTG GAT                      1022
Pro Asp Leu Asp Ala Gly Val Ser Glu His Ser Gly Asp Trp Leu Asp
         225                  230                  235

CAG GAT TCA GTT TCA GAT CAG TTT AGT GTA GAA TTT GAA GTT GAA TCT                      1070
Gln Asp Ser Val Ser Asp Gln Phe Ser Val Glu Phe Glu Val Glu Ser
     240                  245                  250

CTC GAC TCA GAA GAT TAT AGC CTT AGT GAA GAA GGA CAA GAA CTC TCA                      1118
Leu Asp Ser Glu Asp Tyr Ser Leu Ser Glu Glu Gly Gln Glu Leu Ser
255                  260                  265

GAT GAA GAT GAT GAG GTA TAT CAA GTT ACT GTG TAT CAG GCA GGG GAG                      1166
Asp Glu Asp Asp Glu Val Tyr Gln Val Thr Val Tyr Gln Ala Gly Glu
270                  275                  280                  285

AGT GAT ACA GAT TCA TTT GAA GAA GAT CCT GAA ATT TCC TTA GCT GAC                      1214
Ser Asp Thr Asp Ser Phe Glu Glu Asp Pro Glu Ile Ser Leu Ala Asp
             290                  295                  300

TAT TGG AAA TGC ACT TCA TGC AAT GAA ATG AAT CCC CCC CTT CCA TCA                      1262
Tyr Trp Lys Cys Thr Ser Cys Asn Glu Met Asn Pro Pro Leu Pro Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 305 |     |     |     | 310 |     |     |     |     | 315 |     |     |     |     |      |
| CAT | TGC | AAC | AGA | TGT | TGG | GCC | CTT | CGT | GAG | AAT | TGG | CTT | CCT | GAA | GAT | 1310 |
| His | Cys | Asn | Arg | Cys | Trp | Ala | Leu | Arg | Glu | Asn | Trp | Leu | Pro | Glu | Asp |      |
|     |     | 320 |     |     |     | 325 |     |     |     |     | 330 |     |     |     |     |      |
| AAA | GGG | AAA | GAT | AAA | GGG | GAA | ATC | TCT | GAG | AAA | GCC | AAA | CTG | GAA | AAC | 1358 |
| Lys | Gly | Lys | Asp | Lys | Gly | Glu | Ile | Ser | Glu | Lys | Ala | Lys | Leu | Glu | Asn |      |
|     |     | 335 |     |     |     | 340 |     |     |     |     | 345 |     |     |     |     |      |
| TCA | ACA | CAA | GCT | GAA | GAG | GGC | TTT | GAT | GTT | CCT | GAT | TGT | AAA | AAA | ACT | 1406 |
| Ser | Thr | Gln | Ala | Glu | Glu | Gly | Phe | Asp | Val | Pro | Asp | Cys | Lys | Lys | Thr |      |
| 350 |     |     |     |     | 355 |     |     |     |     | 360 |     |     |     |     | 365 |      |
| ATA | GTG | AAT | GAT | TCC | AGA | GAG | TCA | TGT | GTT | GAG | GAA | AAT | GAT | GAT | AAA | 1454 |
| Ile | Val | Asn | Asp | Ser | Arg | Glu | Ser | Cys | Val | Glu | Glu | Asn | Asp | Asp | Lys |      |
|     |     |     |     | 370 |     |     |     |     | 375 |     |     |     |     | 380 |     |      |
| ATT | ACA | CAA | GCT | TCA | CAA | TCA | CAA | GAA | AGT | GAA | GAC | TAT | TCT | CAG | CCA | 1502 |
| Ile | Thr | Gln | Ala | Ser | Gln | Ser | Gln | Glu | Ser | Glu | Asp | Tyr | Ser | Gln | Pro |      |
|     |     |     | 385 |     |     |     |     | 390 |     |     |     |     | 395 |     |     |      |
| TCA | ACT | TCT | AGT | AGC | ATT | ATT | TAT | AGC | AGC | CAA | GAA | GAT | GTG | AAA | GAG | 1550 |
| Ser | Thr | Ser | Ser | Ser | Ile | Ile | Tyr | Ser | Ser | Gln | Glu | Asp | Val | Lys | Glu |      |
|     |     |     | 400 |     |     |     |     | 405 |     |     |     |     | 410 |     |     |      |
| TTT | GAA | AGG | GAA | GAA | ACC | CAA | GAC | AAA | GAA | GAG | AGT | GTG | GAA | TCT | AGT | 1598 |
| Phe | Glu | Arg | Glu | Glu | Thr | Gln | Asp | Lys | Glu | Glu | Ser | Val | Glu | Ser | Ser |      |
|     |     | 415 |     |     |     | 420 |     |     |     |     | 425 |     |     |     |     |      |
| TTG | CCC | CTT | AAT | GCC | ATT | GAA | CCT | TGT | GTG | ATT | TGT | CAA | GGT | CGA | CCT | 1646 |
| Leu | Pro | Leu | Asn | Ala | Ile | Glu | Pro | Cys | Val | Ile | Cys | Gln | Gly | Arg | Pro |      |
| 430 |     |     |     |     | 435 |     |     |     |     | 440 |     |     |     |     | 445 |      |
| AAA | AAT | GGT | TGC | ATT | GTC | CAT | GGC | AAA | ACA | GGA | CAT | CTT | ATG | GCC | TGC | 1694 |
| Lys | Asn | Gly | Cys | Ile | Val | His | Gly | Lys | Thr | Gly | His | Leu | Met | Ala | Cys |      |
|     |     |     |     | 450 |     |     |     |     | 455 |     |     |     |     | 460 |     |      |
| TTT | ACA | TGT | GCA | AAG | AAG | CTA | AAG | AAA | AGG | AAT | AAG | CCC | TGC | CCA | GTA | 1742 |
| Phe | Thr | Cys | Ala | Lys | Lys | Leu | Lys | Lys | Arg | Asn | Lys | Pro | Cys | Pro | Val |      |
|     |     |     | 465 |     |     |     |     | 470 |     |     |     |     | 475 |     |     |      |
| TGT | AGA | CAA | CCA | ATT | CAA | ATG | ATT | GTG | CTA | ACT | TAT | TTC | CCC |     |     | 1784 |
| Cys | Arg | Gln | Pro | Ile | Gln | Met | Ile | Val | Leu | Thr | Tyr | Phe | Pro |     |     |      |
|     |     |     | 480 |     |     |     |     | 485 |     |     |     |     | 490 |     |     |      |

| | | | | |
|-|-|-|-|-|
| TAGTTGACCT | GTCTATAAGA | GAATTATATA | TTTCTAACTA | TATAACCCTA GGAATTTAGA | 1844 |
| CAACCTGAAA | TTTATTCACA | TATATCAAAG | TGAGAAAATG | CCTCAATTCA CATAGATTTC | 1904 |
| TTCTCTTTAG | TATAATTGAC | CTACTTTGGT | AGTGGAATAG | TGAATACTTA CTATAATTTG | 1964 |
| ACTTGAATAT | GTAGCTCATC | CTTTACACCA | ACTCCTAATT | TTAAATAATT TCTACTCTGT | 2024 |
| CTTAAATGAG | AAGTACTTGG | TTTTTTTTTT | CTTAAATATG | TATATGACAT TAAATGTAA | 2084 |
| CTTATTATTT | TTTTGAGAC | CGAGTCTTGC | TCTGTTACCC | AGGCTGGAGT GCAGTGGGTG | 2144 |
| ATCTTGGCTC | ACTGCAAGCT | CTGCCCTCCC | CGGGTTCGCA | CCATTCTCCT GCCTCAGCCT | 2204 |
| CCCAATTAGC | TTGGCCTACA | GTCATCTGCC | ACCACACCTG | GCTAATTTTT TGTACTTTTA | 2264 |
| GTAGAGACAG | GGTTTCACCG | TGTTAGCCAG | GATGGTCTCG | ATCTCCTGAC CTCGTGATCC | 2324 |
| GCCCACCTCG | GCCTCCCAAA | GTGCTGGGAT | TACAGGCATG | AGCCACCG | 2372 |

( 2 ) INFORMATION FOR SEQ ID NO:3:

( i ) SEQUENCE CHARACTERISTICS:
       ( A ) LENGTH: 491 amino acids
       ( B ) TYPE: amino acid
       ( D ) TOPOLOGY: linear ( i i ) MOLECULE TYPE: protein ( x i ) SEQUENCE DESCRIPTION: SEQ ID NO:3:

| Met | Cys | Asn | Thr | Asn | Met | Ser | Val | Pro | Thr | Asp | Gly | Ala | Val | Thr | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
Ser Gln Ile Pro Ala Ser Glu Gln Glu Thr Leu Val Arg Pro Lys Pro
            20              25                  30
Leu Leu Leu Lys Leu Leu Lys Ser Val Gly Ala Gln Lys Asp Thr Tyr
        35              40                  45
Thr Met Lys Glu Val Leu Phe Tyr Leu Gly Gln Tyr Ile Met Thr Lys
    50              55                  60
Arg Leu Tyr Asp Glu Lys Gln Gln His Ile Val Tyr Cys Ser Asn Asp
65              70              75                      80
Leu Leu Gly Asp Leu Phe Gly Val Pro Ser Phe Ser Val Lys Glu His
            85              90                  95
Arg Lys Ile Tyr Thr Met Ile Tyr Arg Asn Leu Val Val Val Asn Gln
            100             105                 110
Gln Glu Ser Ser Asp Ser Gly Thr Ser Val Ser Glu Asn Arg Cys His
        115             120                 125
Leu Glu Gly Gly Ser Asp Gln Lys Asp Leu Val Gln Glu Leu Gln Glu
    130             135                 140
Glu Lys Pro Ser Ser Ser His Leu Val Ser Arg Pro Ser Thr Ser Ser
145             150             155                     160
Arg Arg Arg Ala Ile Ser Glu Thr Glu Glu Asn Ser Asp Glu Leu Ser
            165             170                 175
Gly Glu Arg Gln Arg Lys Arg His Lys Ser Asp Ser Ile Ser Leu Ser
            180             185                 190
Phe Asp Glu Ser Leu Ala Leu Cys Val Ile Arg Glu Ile Cys Cys Glu
        195             200                 205
Arg Ser Ser Ser Ser Glu Ser Thr Gly Thr Pro Ser Asn Pro Asp Leu
    210             215                 220
Asp Ala Gly Val Ser Glu His Ser Gly Asp Trp Leu Asp Gln Asp Ser
225             230             235                     240
Val Ser Asp Gln Phe Ser Val Glu Phe Glu Val Glu Ser Leu Asp Ser
            245             250                 255
Glu Asp Tyr Ser Leu Ser Glu Glu Gly Gln Glu Leu Ser Asp Glu Asp
            260             265                 270
Asp Glu Val Tyr Gln Val Thr Val Tyr Gln Ala Gly Glu Ser Asp Thr
        275             280                 285
Asp Ser Phe Glu Glu Asp Pro Glu Ile Ser Leu Ala Asp Tyr Trp Lys
    290             295                 300
Cys Thr Ser Cys Asn Glu Met Asn Pro Pro Leu Pro Ser His Cys Asn
305             310             315                     320
Arg Cys Trp Ala Leu Arg Glu Asn Trp Leu Pro Glu Asp Lys Gly Lys
            325             330                 335
Asp Lys Gly Glu Ile Ser Glu Lys Ala Lys Leu Glu Asn Ser Thr Gln
            340             345                 350
Ala Glu Glu Gly Phe Asp Val Pro Asp Cys Lys Lys Thr Ile Val Asn
        355             360                 365
Asp Ser Arg Glu Ser Cys Val Glu Glu Asn Asp Asp Lys Ile Thr Gln
    370             375                 380
Ala Ser Gln Ser Gln Glu Ser Glu Asp Tyr Ser Gln Pro Ser Thr Ser
385             390             395                     400
Ser Ser Ile Ile Tyr Ser Ser Gln Glu Asp Val Lys Glu Phe Glu Arg
            405             410                 415
Glu Glu Thr Gln Asp Lys Glu Glu Ser Val Glu Ser Ser Leu Pro Leu
        420             425                 430
Asn Ala Ile Glu Pro Cys Val Ile Cys Gln Gly Arg Pro Lys Asn Gly
```

|       |       |       |       | 435   |       |       |       |       | 440   |       |       |       |       | 445   |       |
|-------|-------|-------|-------|-------|-------|-------|-------|-------|-------|-------|-------|-------|-------|-------|-------|
| Cys   | Ile   | Val   | His   | Gly   | Lys   | Thr   | Gly   | His   | Leu   | Met   | Ala   | Cys   | Phe   | Thr   | Cys   |
|       |       | 450   |       |       |       |       | 455   |       |       |       | 460   |       |       |       |       |
| Ala   | Lys   | Lys   | Leu   | Lys   | Lys   | Arg   | Asn   | Lys   | Pro   | Cys   | Pro   | Val   | Cys   | Arg   | Gln   |
| 465   |       |       |       |       | 470   |       |       |       |       | 475   |       |       |       |       | 480   |
| Pro   | Ile   | Gln   | Met   | Ile   | Val   | Leu   | Thr   | Tyr   | Phe   | Pro   |       |       |       |       |       |
|       |       |       |       | 485   |       |       |       |       | 490   |       |       |       |       |       |       |

( 2 ) INFORMATION FOR SEQ ID NO:4:

( i ) SEQUENCE CHARACTERISTICS:
        ( A ) LENGTH: 1710 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mus musculus ( i x ) FEATURE:
        ( A ) NAME/KEY: CDS
        ( B ) LOCATION: 202..1668

( x i ) SEQUENCE DESCRIPTION: SEQ ID NO:4:

| GAGGAGCCGC | CGCCTTCTCG | TCGCTCGAGC | TCTGGACGAC | CATGGTCGCT | CAGGCCCCGT | 60 |
|---|---|---|---|---|---|---|
| CCGCGGGGCC | TCCGCGCTCC | CCGTGAAGGG | TCGGAAGATG | CGCGGGAAGT | AGCAGCCGTC | 120 |
| TGCTGGGCGA | GCGGGAGACC | GACCGGACAC | CCCTGGGGGA | CCCTCTCGGA | TCACCGCGCT | 180 |

| TCTCCTGCGG | CCTCCAGGCC | A | ATG | TGC | AAT | ACC | AAC | ATG | TCT | GTG | TCT | ACC | 231 |
|---|---|---|---|---|---|---|---|---|---|---|---|---|---|
|   |   |   | Met | Cys | Asn | Thr | Asn | Met | Ser | Val | Ser | Thr |   |
|   |   |   | 1   |     |     |     | 5   |     |     |     |     | 10  |   |

| GAG | GGT | GCT | GCA | AGC | ACC | TCA | CAG | ATT | CCA | GCT | TCG | GAA | CAA | GAG | ACT | 279 |
|---|---|---|---|---|---|---|---|---|---|---|---|---|---|---|---|---|
| Glu | Gly | Ala | Ala | Ser | Thr | Ser | Gln | Ile | Pro | Ala | Ser | Glu | Gln | Glu | Thr |   |
|     |     |     |     | 15  |     |     |     |     | 20  |     |     |     |     | 25  |     |   |

| CTG | GTT | AGA | CCA | AAA | CCA | TTG | CTT | TTG | AAG | TTG | TTA | AAG | TCC | GTT | GGA | 327 |
|---|---|---|---|---|---|---|---|---|---|---|---|---|---|---|---|---|
| Leu | Val | Arg | Pro | Lys | Pro | Leu | Leu | Leu | Lys | Leu | Leu | Lys | Ser | Val | Gly |   |
|     |     |     | 30  |     |     |     |     | 35  |     |     |     |     | 40  |     |     |   |

| GCG | CAA | AAC | GAC | ACT | TAC | ACT | ATG | AAA | GAG | ATT | ATA | TTT | TAT | ATT | GGC | 375 |
|---|---|---|---|---|---|---|---|---|---|---|---|---|---|---|---|---|
| Ala | Gln | Asn | Asp | Thr | Tyr | Thr | Met | Lys | Glu | Ile | Ile | Phe | Tyr | Ile | Gly |   |
|     |     |     | 45  |     |     |     |     | 50  |     |     |     |     | 55  |     |     |   |

| CAG | TAT | ATT | ATG | ACT | AAG | AGG | TTA | TAT | GAC | GAG | AAG | CAG | CAG | CAC | ATT | 423 |
|---|---|---|---|---|---|---|---|---|---|---|---|---|---|---|---|---|
| Gln | Tyr | Ile | Met | Thr | Lys | Arg | Leu | Tyr | Asp | Glu | Lys | Gln | Gln | His | Ile |   |
|     |     | 60  |     |     |     |     | 65  |     |     |     |     | 70  |     |     |     |   |

| GTG | TAT | TGT | TCA | AAT | GAT | CTC | CTA | GGA | GAT | GTG | TTT | GGA | GTC | CCG | AGT | 471 |
|---|---|---|---|---|---|---|---|---|---|---|---|---|---|---|---|---|
| Val | Tyr | Cys | Ser | Asn | Asp | Leu | Leu | Gly | Asp | Val | Phe | Gly | Val | Pro | Ser |   |
| 75  |     |     |     |     | 80  |     |     |     |     | 85  |     |     |     |     | 90  |   |

| TTC | TCT | GTG | AAG | GAG | CAC | AGG | AAA | ATA | TAT | GCA | ATG | ATC | TAC | AGA | AAT | 519 |
|---|---|---|---|---|---|---|---|---|---|---|---|---|---|---|---|---|
| Phe | Ser | Val | Lys | Glu | His | Arg | Lys | Ile | Tyr | Ala | Met | Ile | Tyr | Arg | Asn |   |
|     |     |     |     | 95  |     |     |     |     | 100 |     |     |     |     | 105 |     |   |

| TTA | GTG | GCT | GTA | AGT | CAG | CAA | GAC | TCT | GGC | ACA | TCG | CTG | AGT | GAG | AGC | 567 |
|---|---|---|---|---|---|---|---|---|---|---|---|---|---|---|---|---|
| Leu | Val | Ala | Val | Ser | Gln | Gln | Asp | Ser | Gly | Thr | Ser | Leu | Ser | Glu | Ser |   |
|     |     |     | 110 |     |     |     |     | 115 |     |     |     |     | 120 |     |     |   |

| AGA | CGT | CAG | CCT | GAA | GGT | GGG | AGT | GAT | CTG | AAG | GAT | CCT | TTG | CAA | GCG | 615 |
|---|---|---|---|---|---|---|---|---|---|---|---|---|---|---|---|---|
| Arg | Arg | Gln | Pro | Glu | Gly | Gly | Ser | Asp | Leu | Lys | Asp | Pro | Leu | Gln | Ala |   |
|     |     | 125 |     |     |     |     | 130 |     |     |     |     | 135 |     |     |     |   |

| CCA | CCA | GAA | GAG | AAA | CCT | TCA | TCT | TCT | GAT | TTA | ATT | TCT | AGA | CTG | TCT | 663 |
|---|---|---|---|---|---|---|---|---|---|---|---|---|---|---|---|---|
| Pro | Pro | Glu | Glu | Lys | Pro | Ser | Ser | Ser | Asp | Leu | Ile | Ser | Arg | Leu | Ser |   |
|     | 140 |     |     |     |     | 145 |     |     |     |     | 150 |     |     |     |     |   |

| | | | | | | | | | | | | | | | | |
|---|---|---|---|---|---|---|---|---|---|---|---|---|---|---|---|---|
| ACC | TCA | TCT | AGA | AGG | AGA | TCC | ATT | AGT | GAG | ACA | GAA | GAG | AAC | ACA | GAT | 711 |
| Thr | Ser | Ser | Arg | Arg | Arg | Ser | Ile | Ser | Glu | Thr | Glu | Glu | Asn | Thr | Asp | |
| 155 | | | | | 160 | | | | 165 | | | | | | 170 | |
| GAG | CTA | CCT | GGG | GAG | CGG | CAC | CGG | AAG | CGC | CGC | AGG | TCC | CTG | TCC | TTT | 759 |
| Glu | Leu | Pro | Gly | Glu | Arg | His | Arg | Lys | Arg | Arg | Arg | Ser | Leu | Ser | Phe | |
| | | | | 175 | | | | | 180 | | | | | 185 | | |
| GAT | CCG | AGC | CTG | GGT | CTG | TGT | GAG | CTG | AGG | GAG | ATG | TGC | AGC | GGC | GGC | 807 |
| Asp | Pro | Ser | Leu | Gly | Leu | Cys | Glu | Leu | Arg | Glu | Met | Cys | Ser | Gly | Gly | |
| | | | | 190 | | | | | 195 | | | | | 200 | | |
| ACG | AGC | AGC | AGT | AGC | AGC | AGC | AGC | GAG | TCC | ACA | GAG | ACG | CCC | TCG | | 855 |
| Thr | Ser | Ser | Ser | Ser | Ser | Ser | Ser | Glu | Ser | Thr | Glu | Thr | Pro | Ser | | |
| | | | 205 | | | | | 210 | | | | 215 | | | | |
| CAT | CAG | GAT | CTT | GAC | GAT | GGC | GTA | AGT | GAG | CAT | TCT | GGT | GAT | TGC | CTG | 903 |
| His | Gln | Asp | Leu | Asp | Asp | Gly | Val | Ser | Glu | His | Ser | Gly | Asp | Cys | Leu | |
| 220 | | | | | 225 | | | | | 230 | | | | | | |
| GAT | CAG | GAT | TCA | GTT | TCT | GAT | CAG | TTT | AGC | GTG | GAA | TTT | GAA | GTT | GAG | 951 |
| Asp | Gln | Asp | Ser | Val | Ser | Asp | Gln | Phe | Ser | Val | Glu | Phe | Glu | Val | Glu | |
| 235 | | | | | 240 | | | | | 245 | | | | | 250 | |
| TCT | CTG | GAC | TCG | GAA | GAT | TAC | AGC | CTG | AGT | GAC | GAA | GGG | CAC | GAG | CTC | 999 |
| Ser | Leu | Asp | Ser | Glu | Asp | Tyr | Ser | Leu | Ser | Asp | Glu | Gly | His | Glu | Leu | |
| | | | | 255 | | | | | 260 | | | | | 265 | | |
| TCA | GAT | GAG | GAT | GAT | GAG | GTC | TAT | CGG | GTC | ACA | GTC | TAT | CAG | ACA | GGA | 1047 |
| Ser | Asp | Glu | Asp | Asp | Glu | Val | Tyr | Arg | Val | Thr | Val | Tyr | Gln | Thr | Gly | |
| | | | 270 | | | | | 275 | | | | | 280 | | | |
| GAA | AGC | GAT | ACA | GAC | TCT | TTT | GAA | GGA | GAT | CCT | GAG | ATT | TCC | TTA | GCT | 1095 |
| Glu | Ser | Asp | Thr | Asp | Ser | Phe | Glu | Gly | Asp | Pro | Glu | Ile | Ser | Leu | Ala | |
| | | | 285 | | | | | 290 | | | | | 295 | | | |
| GAC | TAT | TGG | AAG | TGT | ACC | TCA | TGC | AAT | GAA | ATG | AAT | CCT | CCC | CTT | CCA | 1143 |
| Asp | Tyr | Trp | Lys | Cys | Thr | Ser | Cys | Asn | Glu | Met | Asn | Pro | Pro | Leu | Pro | |
| | | 300 | | | | | 305 | | | | | 310 | | | | |
| TCA | CAC | TGC | AAA | AGA | TGC | TGG | ACC | CTT | CGT | GAG | AAC | TGG | CTT | CCA | GAC | 1191 |
| Ser | His | Cys | Lys | Arg | Cys | Trp | Thr | Leu | Arg | Glu | Asn | Trp | Leu | Pro | Asp | |
| 315 | | | | | 320 | | | | | 325 | | | | | 330 | |
| GAT | AAG | GGG | AAA | GAT | AAA | GTG | GAA | ATC | TCT | GAA | AAA | GCC | AAA | CTG | GAA | 1239 |
| Asp | Lys | Gly | Lys | Asp | Lys | Val | Glu | Ile | Ser | Glu | Lys | Ala | Lys | Leu | Glu | |
| | | | | 335 | | | | | 340 | | | | | 345 | | |
| AAC | TCA | GCT | CAG | GCA | GAA | GAA | GGC | TTG | GAT | GTG | CCT | GAT | GGC | AAA | AAG | 1287 |
| Asn | Ser | Ala | Gln | Ala | Glu | Glu | Gly | Leu | Asp | Val | Pro | Asp | Gly | Lys | Lys | |
| | | | 350 | | | | | 355 | | | | | 360 | | | |
| CTG | ACA | GAG | AAT | GAT | GCT | AAA | GAG | CCA | TGT | GCT | GAG | GAG | GAC | AGC | GAG | 1335 |
| Leu | Thr | Glu | Asn | Asp | Ala | Lys | Glu | Pro | Cys | Ala | Glu | Glu | Asp | Ser | Glu | |
| | | 365 | | | | | 370 | | | | | 375 | | | | |
| GAG | AAG | GCC | GAA | CAG | ACG | CCC | CTG | TCC | CAG | GAG | AGT | GAC | GAC | TAT | TCC | 1383 |
| Glu | Lys | Ala | Glu | Gln | Thr | Pro | Leu | Ser | Gln | Glu | Ser | Asp | Asp | Tyr | Ser | |
| | 380 | | | | | 385 | | | | | 390 | | | | | |
| CAA | CCA | TCG | ACT | TCC | AGC | AGC | ATT | GTT | TAT | AGC | AGC | CAA | GAA | AGC | GTG | 1431 |
| Gln | Pro | Ser | Thr | Ser | Ser | Ser | Ile | Val | Tyr | Ser | Ser | Gln | Glu | Ser | Val | |
| 395 | | | | | 400 | | | | | 405 | | | | | 410 | |
| AAA | GAG | TTG | AAG | GAG | GAA | ACG | CAG | CAC | AAA | GAC | GAG | AGT | GTG | GAA | TCT | 1479 |
| Lys | Glu | Leu | Lys | Glu | Glu | Thr | Gln | His | Lys | Asp | Glu | Ser | Val | Glu | Ser | |
| | | | | 415 | | | | | 420 | | | | | 425 | | |
| AGC | TTC | TCC | CTG | AAT | GCC | ATC | GAA | CCA | TGT | GTG | ATC | TGC | CAG | GGG | CGG | 1527 |
| Ser | Phe | Ser | Leu | Asn | Ala | Ile | Glu | Pro | Cys | Val | Ile | Cys | Gln | Gly | Arg | |
| | | | 430 | | | | | 435 | | | | | 440 | | | |
| CCT | AAA | AAT | GGC | TGC | ATT | GTT | CAC | GGC | AAG | ACT | GGA | CAC | CTC | ATG | TCA | 1575 |
| Pro | Lys | Asn | Gly | Cys | Ile | Val | His | Gly | Lys | Thr | Gly | His | Leu | Met | Ser | |
| | | 445 | | | | | 450 | | | | | 455 | | | | |
| TGT | TTC | ACG | TGT | GCA | AAG | AAG | CTA | AAA | AAA | AGA | AAC | AAG | CCC | TGC | CCA | 1623 |
| Cys | Phe | Thr | Cys | Ala | Lys | Lys | Leu | Lys | Lys | Arg | Asn | Lys | Pro | Cys | Pro | |
| | 460 | | | | | 465 | | | | | 470 | | | | | |

```
GTG  TGC  AGA  CAG  CCA  ATC  CAA  ATG  ATT  GTG  CTA  AGT  TAC  TTC  AAC        1668
Val  Cys  Arg  Gln  Pro  Ile  Gln  Met  Ile  Val  Leu  Ser  Tyr  Phe  Asn
475                 480                      485

TAGCTGACCT GCTCACAAAA ATAGAATTTT ATATTTCTAA CT                                    1710
```

( 2 ) INFORMATION FOR SEQ ID NO:5:

( i ) SEQUENCE CHARACTERISTICS:
        ( A ) LENGTH: 489 amino acids
        ( B ) TYPE: amino acid
        ( D ) TOPOLOGY: linear ( ii ) MOLECULE TYPE: protein ( x i ) SEQUENCE DESCRIPTION: SEQ ID NO:5:

```
Met  Cys  Asn  Thr  Asn  Met  Ser  Val  Ser  Thr  Glu  Gly  Ala  Ala  Ser  Thr
1                   5                        10                       15

Ser  Gln  Ile  Pro  Ala  Ser  Glu  Gln  Thr  Leu  Val  Arg  Pro  Lys  Pro
               20                  25                       30

Leu  Leu  Leu  Lys  Leu  Leu  Lys  Ser  Val  Gly  Ala  Gln  Asn  Asp  Thr  Tyr
               35                  40                       45

Thr  Met  Lys  Glu  Ile  Ile  Phe  Tyr  Ile  Gly  Gln  Tyr  Ile  Met  Thr  Lys
     50                       55                       60

Arg  Leu  Tyr  Asp  Glu  Lys  Gln  Gln  His  Ile  Val  Tyr  Cys  Ser  Asn  Asp
65                       70                       75                       80

Leu  Leu  Gly  Asp  Val  Phe  Gly  Val  Pro  Ser  Phe  Ser  Val  Lys  Glu  His
                    85                       90                       95

Arg  Lys  Ile  Tyr  Ala  Met  Ile  Tyr  Arg  Asn  Leu  Val  Ala  Val  Ser  Gln
               100                      105                      110

Gln  Asp  Ser  Gly  Thr  Ser  Leu  Ser  Glu  Ser  Arg  Arg  Gln  Pro  Glu  Gly
               115                      120                      125

Gly  Ser  Asp  Leu  Lys  Asp  Pro  Leu  Gln  Ala  Pro  Pro  Glu  Glu  Lys  Pro
     130                      135                      140

Ser  Ser  Ser  Asp  Leu  Ile  Ser  Arg  Leu  Ser  Thr  Ser  Ser  Arg  Arg  Arg
145                      150                      155                      160

Ser  Ile  Ser  Glu  Thr  Glu  Glu  Asn  Thr  Asp  Glu  Leu  Pro  Gly  Glu  Arg
                    165                      170                      175

His  Arg  Lys  Arg  Arg  Arg  Ser  Leu  Ser  Phe  Asp  Pro  Ser  Leu  Gly  Leu
               180                      185                      190

Cys  Glu  Leu  Arg  Glu  Met  Cys  Ser  Gly  Gly  Thr  Ser  Ser  Ser  Ser  Ser
          195                      200                      205

Ser  Ser  Ser  Glu  Ser  Thr  Glu  Thr  Pro  Ser  His  Gln  Asp  Leu  Asp  Asp
     210                      215                      220

Gly  Val  Ser  Glu  His  Ser  Gly  Asp  Cys  Leu  Asp  Gln  Asp  Ser  Val  Ser
225                      230                      235                      240

Asp  Gln  Phe  Ser  Val  Glu  Phe  Glu  Val  Glu  Ser  Leu  Asp  Ser  Glu  Asp
                    245                      250                      255

Tyr  Ser  Leu  Ser  Asp  Glu  Gly  His  Glu  Leu  Ser  Asp  Glu  Asp  Asp  Glu
               260                      265                      270

Val  Tyr  Arg  Val  Thr  Val  Tyr  Gln  Thr  Gly  Glu  Ser  Asp  Thr  Asp  Ser
          275                      280                      285

Phe  Glu  Gly  Asp  Pro  Glu  Ile  Ser  Leu  Ala  Asp  Tyr  Trp  Lys  Cys  Thr
     290                      295                      300

Ser  Cys  Asn  Glu  Met  Asn  Pro  Pro  Leu  Pro  Ser  His  Cys  Lys  Arg  Cys
305                      310                      315                      320

Trp  Thr  Leu  Arg  Glu  Asn  Trp  Leu  Pro  Asp  Asp  Lys  Gly  Lys  Asp  Lys
```

|     |     |     |     | 325 |     |     |     |     |     |     |     | 330 |     |     |     | 335 |     |
|-----|-----|-----|-----|-----|-----|-----|-----|-----|-----|-----|-----|-----|-----|-----|-----|-----|-----|
| Val | Glu | Ile | Ser | Glu | Lys | Ala | Lys | Leu | Glu | Asn | Ser | Ala | Gln | Ala | Glu |     |     |
|     |     |     | 340 |     |     |     |     | 345 |     |     |     |     | 350 |     |     |     |     |
| Glu | Gly | Leu | Asp | Val | Pro | Asp | Gly | Lys | Lys | Leu | Thr | Glu | Asn | Asp | Ala |     |     |
|     |     | 355 |     |     |     |     | 360 |     |     |     |     | 365 |     |     |     |     |     |
| Lys | Glu | Pro | Cys | Ala | Glu | Glu | Asp | Ser | Glu | Glu | Lys | Ala | Glu | Gln | Thr |     |     |
|     | 370 |     |     |     |     | 375 |     |     |     |     | 380 |     |     |     |     |     |     |
| Pro | Leu | Ser | Gln | Glu | Ser | Asp | Asp | Tyr | Ser | Gln | Pro | Ser | Thr | Ser | Ser |     |     |
| 385 |     |     |     |     | 390 |     |     |     |     | 395 |     |     |     |     | 400 |     |     |
| Ser | Ile | Val | Tyr | Ser | Ser | Gln | Glu | Ser | Val | Lys | Glu | Leu | Lys | Glu | Glu |     |     |
|     |     |     |     | 405 |     |     |     |     | 410 |     |     |     |     | 415 |     |     |     |
| Thr | Gln | His | Lys | Asp | Glu | Ser | Val | Glu | Ser | Ser | Phe | Ser | Leu | Asn | Ala |     |     |
|     |     |     | 420 |     |     |     |     | 425 |     |     |     |     | 430 |     |     |     |     |
| Ile | Glu | Pro | Cys | Val | Ile | Cys | Gln | Gly | Arg | Pro | Lys | Asn | Gly | Cys | Ile |     |     |
|     |     | 435 |     |     |     |     | 440 |     |     |     |     | 445 |     |     |     |     |     |
| Val | His | Gly | Lys | Thr | Gly | His | Leu | Met | Ser | Cys | Phe | Thr | Cys | Ala | Lys |     |     |
|     | 450 |     |     |     |     | 455 |     |     |     |     | 460 |     |     |     |     |     |     |
| Lys | Leu | Lys | Lys | Arg | Asn | Lys | Pro | Cys | Pro | Val | Cys | Arg | Gln | Pro | Ile |     |     |
| 465 |     |     |     |     | 470 |     |     |     |     | 475 |     |     |     |     | 480 |     |     |
| Gln | Met | Ile | Val | Leu | Ser | Tyr | Phe | Asn |     |     |     |     |     |     |     |     |     |
|     |     |     |     | 485 |     |     |     |     |     |     |     |     |     |     |     |     |     |

ANTIBODIES FOR DETECTION OF HUMAN MDM2 PROTEIN

This invention was made with support from the U.S. Government, including NIH grants CA-57345, CA-43460, CA-02243 and CA-35494. Accordingly, the Government retains certain rights in the invention.

This application is a division of application Ser. No. 08/044,619 filed Apr. 7, 1993, now U.S. Pat. 5,420,263, which is a continuation-in-part of Ser. No. 07/903,103, filed Jun. 23, 1992, now U.S. Pat. No. 5,411,619, which is a continuation in part of Ser. No. 07/867,840 filed Apr. 7, 1992, abandoned.

FIELD OF THE INVENTION

The invention relates to the area of cancer diagnostics and therapeutics. More particularly, the invention relates to the detection of a gene which is amplified in certain human tumors.

BACKGROUND OF THE INVENTION

According to the Knudson model for tumorigenesis (Cancer Research, 1985, vol. 45, p. 1482), there are tumor suppressor genes in all normal cells which, when they become non-functional due to mutation, cause neoplastic development. Evidence for this model has been found in cases of retinoblastoma and colorectal tumors. The implicated suppressor genes in these tumors, RB and p53 respectively, were found to be deleted or altered in many of the tumors studied.

The p53 gene product, therefore, appears to be a member of a group of proteins which regulate normal cellular proliferation and suppression of cellular transformation. Mutations in the p53 gene have been linked to tumorigenesis, suggesting that alterations in p53 protein function are involved in cellular transformation. The inactivation of the p53 gene has been implicated in the genesis or progression of a wide variety of carcinomas (Nigro et al., 1989, *Nature* 342:705–708), including human colorectal carcinoma (Baker et al., 1989, *Science* 244:217–221), human lung cancer (Takahashi et al., 1989, *Science* 246:491–494; Iggo et al., 1990, *Lancet* 335:675–679), chronic myelogenous leukemia (Kelman et al, 1989, *Proc. Natl. Acad. Sci. USA* 86:6783–6787) and osteogenic sarcomas (Masuda et al., 1987, *Proc. Natl. Acad. Sci. USA* 84:7716–7719).

While there exists an enormous body of evidence linking p53 gene mutations to human tumorigenesis (Hollstein et al., 1991, *Science* 253:49–53) little is known about cellular regulators and mediators of p53 function.

Hinds et al. (*Cell Growth & Differentiation*, 1:571–580, 1990), found that p53 cDNA clones, containing a point mutation at amino acid residue 143, 175, 273 or 281, cooperated with the activated ras oncogene to transform primary rat embryo fibroblasts in culture. These mutant p53 genes are representative of the majority of mutations found in human cancer. Hollstein et al., 1991, *Science* 253:49–53. The transformed fibroblasts were found to produce elevated levels of human p53 protein having extended half-lives (1.5 to 7 hours) as compared to the normal (wild-type) p53 protein (20 to 30 minutes).

Mutant p53 proteins with mutations at residue 143 or 175 form an oligomeric protein complex with the cellular heat shock protein hsc70. While residue 273 or 281 mutants do not detectably bind hsc70, and are poorer at producing transformed foci than the 175 mutant, complex formation between mutant p53 and hsc70 is not required for p53-mediated transformation. Complex formation does, however, appear to facilitate this function. All cell lines transformed with the mutant p53 genes are tumorigenic in a thymic (nude) mice. In contrast, the wild-type human p53 gene does not possess transforming activity in cooperation with ras. Tuck and Crawford, 1989, *Oncogene Res.* 481–96.

Hinds et al., supra also expressed human p53 protein in transformed rat cells. When the expressed human p53 was immunoprecipitated with two p53 specific antibodies directed against distinct epitopes of p53, an unidentified $M_r$ 90,000 protein was coimmunoprecipitated. This suggested that the rat $M_r$ 90,000 protein is in a complex with the human p53 protein in the transformed rat cell line.

As mentioned above, levels of p53 protein are often higher in transformed cells than normal cells. This is due to mutations which increase its metabolic stability (Oven et al., 1981, *Mol. Cell. Biol.* 1:101–110; Reich et al. (1983), *Mol. Cell. Biol.* 3:2143–2150). The stabilization of p53 has been associated with complex formation between p53 and viral or cellular proteins. (Linzer and Levine, 1979, *Cell* 17:43–52; Crawford et al., 1981, *Proc. Natl. Acad. Sci. USA* 78:41–45; Dippold et al., 1981, *Proc. Natl. Acad. Sci. USA* 78:1695–1699; Lane and Crawford, 1979, *Nature* (Lond.) 278:261–263; Hinds et al., 1987, *Mol. Cell. Biol.* 7:2863–2869; Finlay et al., 1988, *Mol. Cell. Biol.* 8:531–539; Sarnow et al., 1982, *Cell.* 28:387–394; Gronostajski et al., 1984, *Mol. Cell. Biol.* 4:442–448; Pinhasi-Kimhi et al., 1986, *Nature* (Lond.) 320:182–185; Ruscetti and Scolnick, 1983, *J. Virol.* 46:1022–1026; Pinhasi and Oren, 1984, *Mol. Cell. Biol.* 4:2180–2186; and Sturzbecher et al., 1987, *Oncogene* 1:201–211.) For example, p53 protein has been observed to form oligomeric protein complexes with the SV40 large T antigen, the adenovirus type 5 E1B-$M_r$ 55,000 protein, and the human papilloma virus type 16 or 18 E6 product. Linzer and Levine, 1979, *Cell* 17:43–52; Lane and Crawford, 1979, *Nature*, 278:261–263; Sarnow et al., 1982, *Cell* 28:387–394; Wereess et al., 1990, *Science*, 248:76–79. Similarly, complexes have been observed of p105$^{RB}$ (the product of the retinoblastoma susceptibility gene) with T antigen (DeCaprio et al., 1988, *Cell* 54:275–283), the adenovirus EIA protein (Whyte et al., 1988, *Nature* 334:124–129) and the E7 protein of human papilloma virus 16 or 18 (Münger et al., 1989, *EMBO J.* 8:4099–4105). It has been suggested that interactions between these viral proteins and p105$^{RB}$ inactivate a growth-suppressive function of p 105$^{RB}$, mimicking deletions and mutations commonly found in the RB gene in tumor cells. In a similar fashion, oligomeric protein complex formation between these viral proteins and p53 may eliminate or alter the function of p53. Finlay et al., 1989, *Cell* 5 7:1083–1093.

Fakharzadeh et al. (*EMBO J.* 10:1565–1569, 1991) analyzed amplified DNA sequences present in a tumorigenic mouse cell line (i.e., 3T3DM, a spontaneously transformed derivative of mouse Balb/c cells). Studies were conducted to determine whether any of the amplified genes induced tumorigenicity following introduction of the amplified genes into a nontransformed recipient cell (e.g., mouse NIH3T3 or Rat2 cells). The resulting cell lines were tested for tumorigenicity in nude mice. A gene, designated MDM2, which is amplified more than 50-fold in 3T3DM cells, induced tumorigenicity when overexpressed in NIH3T3 and Rat 2 cells. From the nucleotide and predicted amino acid sequence of mouse MDM2 (mMDM2), Fakharzadeh speculated that this gene encodes a potential DNA binding protein that functions in the modulation of expression of other genes and, when present in excess, interferes with normal constraints on cell growth.

SUMMARY OF THE INVENTION

It is an object of the invention to provide a method for diagnosing a neoplastic tissue, such as sarcoma, in a human.

It is another object of the invention to provide a cDNA molecule encoding the sequence of human MDM2.

Yet another object of the invention is to provide a preparation of human MDM2 protein which is substantially free of other human cellular proteins.

Still another object of the invention is to provide DNA probes capable of hybridizing with human MDM2 genes or mRNA molecules.

Another object of the invention is to provide antibodies immunoreactive with human MDM2 protein.

Still another object of the invention is to provide kits for detecting amplification or elevated expression of human MDM2.

Yet another object of the invention is to provide methods for identifying compounds which interfere with the binding of human MDM2 to human p53.

A further object of the invention is to provide a method of treating a neoplastic human cell.

Yet another object of the invention is to provide methods for inhibiting the growth of tumor cells which contain a human MDM2 gene amplification.

Still another object of the invention is to provide polypeptides which interfere with the binding of human MDM2 to human p53.

A further object of the invention is to provide a method for growing host cells containing a p53 expression vector.

It has now been discovered that hMDM2, a heretofore unknown human gene, plays a role in human cancer. The hMDM2 gene has been cloned and the recombinant derived hMDM2 protein shown to bind to human p53 in vitro. hMDM2 has been found to be amplified in some neoplastic cells and the expression of hMDM2-encoded products has been found to be correspondingly elevated in tumors with amplification of this gene. The elevated levels of MDM2 appear to sequester p53 and allow the cell to escape from p53-regulated growth.

BRIEF DESCRIPTION OF THE DRAWINGS

FIG. 1A, FIG. 1B, and FIG. 1C show the cDNA sequence of human MDM2. In these Figures, human and mouse nucleotide and amino acid sequences are compared, the mouse sequence being shown only where it differs from the corresponding human sequence.

FIG. 2 shows that hMDM2 binds to p53.

FIG. 3 illustrates the amplification of the hMDM2 gene in sarcomas.

FIG. 4A. Northern blot analysis of hMDM2 RNA expression in cell lines.

FIG. 4B. Western blot analysis of hMDM2 protein expression in cell lines.

FIG. 4C. Western blot analysis of hMDM2 protein expression in primary sarcomas.

FIGS. 6A and 6B. Random fragments of MDM2 were fused to sequences encoding the lexA DNA binding domain and the resultant clones transfected into yeast carrying pRS3145N (p53 expression vector) and pJK103 (lexA-responsive β-galactosidase reporter). Yeast clones expressing β-galactosidase were identified by their blue color, and the MDM2 sequences in the lexA fusion vector were determined.

FIG. 6A. In clones expressing the indicated portions of MDM2, expression of β-galactosidase activity was independent of p53 expression.

FIG. 6B. In clones expressing the indicated portions of MDM2, expression of β-galactosidase activity was dependent on p53 expression. The bottom 6 clones in B were generated by genetic engineering.

FIG. 6C. Random fragments of p53 were fused to the sequence encoding the 1342 acidic activation domain and a hemagglutinin epitope tag; the resultant clones were transfected into yeast carrying lexA-MDM2 (lexA DNA binding domain fused to full length MDM2) and pJK103. Yeast clones were identified as above, and all were found to be MDM2-dependent. The bottom three clones were generated by genetic engineering.

DETAILED DESCRIPTION OF THE INVENTION

Figure 4A:
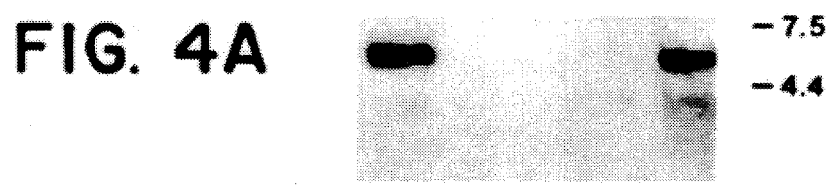
FIG. 4A–C illustrates hMDM2 expression in cell lines and primary sarcomas.

It is a discovery of the present invention that a gene exists which is amplified in some human tumors. The amplification of this gene, designated MDM2, is diagnostic of neoplasia or the potential therefor. Detecting the elevated expression of human MDM2-encoded products is also diagnostic of neoplasia or the potential for neoplastic transformation. Over a third of the sarcomas surveyed, including the most common bone and soft tissue forms, were found to have amplified hMDM2 sequences. Expression of hMDM2 was found to be correspondingly elevated in tumors with the gene amplification.

Other genetic alterations leading to elevated hMDM2 expression may be involved in tumorigenesis also, such as mutations in regulatory regions of the gene. Elevated expression of hMDM2 may also be involved in tumors other than sarcomas including but not limited to those in which p53 inactivation has been implicated. These include colorectal carcinoma, lung cancer and chronic myelogenous leukemia.

According to one embodiment of the invention, a method of diagnosing a neoplastic tissue in a human is provided. Tissue or body fluid is isolated from a human, and the copy number of human MDM2 genes is determined. Alternatively, expression levels of human MDM2 gene products can be determined. These include protein and mRNA.

Body fluids which may be tested include urine, serum, blood, feces, saliva, and the like. Tissues suspected of being neoplastic are desirably separated from normal appearing tissue for analysis. This can be done by paraffin or cryostat sectioning or flow cytometry, as is known in the art. Failure to separate neoplastic from non-neoplastic cells can confound the analysis. Adjacent non-neoplastic tissue or any normal tissue can be used to determine a base-line level of expression or copy number, against which the amount of hMDM2 gene or gene products can be compared.

The human MDM2 gene is considered to be amplified if the cell contains more than the normal copy number (2) of this gene per genome. The various techniques for detecting gene amplification are well known in the art. Gene amplification can be determined, for example, by Southern blot analysis, as described in Example 4, wherein cellular DNA from a human tissue is digested, separated, and transferred to a filter where it is hybridized with a probe containing complementary nucleic acids. Alternatively, quantitative polymerase chain reaction (PCR) employing primers can be used to determine gene amplification. Appropriate primers will bind to sequences that bracket human MDM2 coding sequences. Other techniques for determining gene copy number as are known in the art can be used without limitation.

The gene product which is measured may be either mRNA or protein. The term elevated expression means an increase in mRNA production or protein production over that which is normally produced by non-cancerous cells. Although amplification has been observed in human sarcomas, other genetic alterations leading to elevated expression of MDM2 may be present in these or other tumors. Other tumors include those of lung, breast, brain, colorectal, bladder, prostate, liver, skin, and stomach. These, too, are contemplated by the present invention. Non-cancerous cells for use in determining baseline expression levels can be obtained from cells surrounding a tumor, from other humans or from human cell lines. Any increase can have diagnostic value, but generally the mRNA or protein expression will be elevated at least about 3-fold, 5-fold, and in some cases up to about 100-fold over that found in non-cancerous cells. The particular technique employed for detecting mRNA or protein is not critical to the practice of the invention. Increased production of mRNA or protein may be detected, for example, using the techniques of Northern blot analysis or Western blot analysis, respectively, as described in Example 4 or other known techniques such as ELISA, immunoprecipitation, RIA and the like. These techniques are also well known to the skilled artisan.

According to another embodiment of the invention, nucleic acid probes or primers for the determining of human MDM2 gene amplification or elevated expression of mRNA are provided. The probe may comprise ribo- or deoxyribonucleic acids and may contain the entire human MDM2 coding sequence, a sequence complementary thereto, or fragments thereof. A probe may contain, for example, nucleotides 1–949, or 1–2372 as shown in FIG. 1. Generally, probes or primers will contain at least about 14 contiguous nucleotides of the human sequence but may desirably contain about 40, 50 or 100 nucleotides. Probes are typically labelled with a fluorescent tag, a radioisotope, or the like to render them easily detectable. Preferably the probes will hybridize under stringent hybridization conditions. Under such conditions they will not hybridize to mouse MDM2. The probes of the invention are complementary to the human MDM2 gene. This means that they share 100% identity with the human sequence.

hMDM2 protein can be produced, according to the invention, substantially free of other human proteins. Provided with the DNA sequence, those of skill in the art can express the cDNA in a non-human cell. Lysates of such cells provide proteins substantially free of other human proteins. The lysates can be further purified, for example, by immunoprecipitation, co-precipitation with p53, or by affinity chromatography.

The antibodies of the invention are specifically reactive with hMDM2 protein. Preferably, they do not cross-react with MDM2 from other species. They can be polyclonal or monoclonal, and can be raised against native hMDM2 or a hMDM2 fusion protein or synthetic peptide. The antibodies are specifically immunoreactive with hMDM2 epitopes which are not present on other human proteins. Some antibodies are reactive with epitopes unique to human MDM2 and not present on the mouse homolog. The antibodies are useful in conventional analyses, such as Western blot analysis, ELISA, immunohistochemistry, and other immunological assays for the detection of proteins. Techniques for raising and purifying polyclonal antibodies are well known in the art, as are techniques for preparing monoclonal antibodies. Antibody binding can be determined by methods known in the art, such as use of an enzyme-labelled secondary antibody, staphylococcal protein A, and the like. Certain monoclonal antibodies of the invention were deposited on Mar. 11, 1993 at the American Type Culture Collection, 12301 Parklawn Drive, Rockville, Md. 20852. These include IF2, and ED9, which have been granted accession nos. HB 11290, and HB 11291, respectively.

According to another embodiment of the invention, interference with the expression of MDM2 provides a therapeutic modality. The method can be applied in vivo, in vitro, or ex vivo. For example, expression may be down-regulated by administering triple-strand forming or antisense oligonucleotides which bind to the hMDM2 gene or mRNA, respectively, and prevent transcription or translation. The oligonucleotides may interact with unprocessed pre-mRNA or processed mRNA. Small molecules and peptides which specifically inhibit MDM2 expression can also be used. Similarly, such molecules which inhibit the binding of MDM2 to p53 would be therapeutic by alleviating the sequestration of p53.

Such inhibitory molecules can be identified by screening for interference of the hMDM2/p53 interaction where one of the binding partners is bound to a solid support and the other partner is labeled. Antibodies specific for epitopes on hMDM2 or p53 which are involved in the binding interaction will interfere with such binding. Solid supports which may be used include any polymers which are known to bind proteins. The support may be in the form of a filter, column packing matrix, beads, and the like. Labeling of proteins can be accomplished according to any-technique known in the art. Radiolabels, enzymatic labels, and fluorescent labels can be used advantageously. Alternatively, both hMDM2 and p53 may be in solution and bound molecules separated from unbound subsequently. Any separation technique known in the an may be employed, including immunoprecipitation or immunoaffinity separation with an antibody specific for the unlabeled binding partner.

It has been found that amino acid residues 13-41 of p53 (See SEQ ID NO: 1) are necessary for the interaction of MDM-2 and p53. However, additional residues on either the amino or carboxy terminal side of the peptide appear also to be required. Nine to 13 additional p53 residues are sufficient to achieve MDM2 binding, although less may be necessary. Since cells which overexpress MDM2 escape from p53-regulated growth control in sarcomas, the use of p53-derived peptides to bind to excess MDM2 leads to reestablishment of p53-regulated growth control.

Suitable p53-derived peptides for administration are those which are circular, linear, or derivitized to achieve better penetration of membranes, for example. Other organic compounds which are modelled to achieve the same three dimensional structure as the peptide of the invention can also be used.

DNA encoding the MDM2-binding, p53-derived peptide, or multiple copies thereof, may also be administered to tumor cells as a mode of administering the peptide. The DNA will typically be in an expression construct, such as a retrovirus, DNA virus, or plasmid vector, which has the DNA elements necessary for expression properly positioned to achieve expression of the MDM2-binding peptide. The DNA can be administered, inter alia encapsulated in liposomes, or in any other form known to the art to achieve efficient uptake by cells. As in the direct administration of peptide, the goal is to alleviate the sequestration of p53 by MDM2.

A cDNA molecule containing the coding sequence of hMDM2 can be used to produce probes and primers. In addition, it can be expressed in cultured cells, such as E. coli, to yield preparations of hMDM2 protein substantially free of other human proteins. The proteins produced can be purified, for example, with immunoaffinity techniques using the antibodies described above.

Kits are provided which contain the necessary reagents for determining gene copy number, such as probes or primers specific for the hMDM2 gene, as well as written instructions. The instructions can provide calibration curves to compare with the determined values. Kits are also provided to determine elevated expression of mRNA (i.e., containing probes) or hMDM2 protein (i.e., containing antibodies). Instructions will allow the tester to determine whether the expression levels are elevated. Reaction vessels and auxiliary reagents such as chromogens, buffers, enzymes, etc. may also be included in the kits.

The human MDM2 gene has now been identified and cloned. Recombinant derived hMDM2 has been shown to bind to human p53. Moreover, it has been found that hMDM2 is amplified in some sarcomas. The amplification leads to a corresponding increase in MDM2 gene products. Such amplification is associated with the process of tumorigenesis. This discovery, allows specific assays to be performed to assess the neoplastic or potential neoplastic status of a particular tissue.

The following examples are provided to exemplify various aspects of the invention and are not intended to limit the scope of the invention.

EXAMPLES

Example 1

To obtain human cDNA clones, a cDNA library was screened with a murine MDM2 (mMDM2) cDNA probe. A cDNA library was prepared by using polyadenylated RNA isolated from the human colonic carcinoma cell line CaCo-2 as a template for the production of random hexamer primed double stranded cDNA. Gubler and Hoffmann, 1983, *Gene* 25:263–268. The cDNA was ligated to adaptors and then to the lambda YES phage vector, packaged, and plated as described by Elledge et al. (*Proc. Natl. Acad. Sci. USA*, 88:1731–1735, 1991). The library was screened initially with a P-labelled (Kinzler, K. W., et al., *Nucl. Acids Res.* 17:3645–3653 (1989), Feinberg and Vogelstein, 1983, *Anal. Biochem.* 132:6–13) mMDM2 cDNA probe (nucleotides 259 to 1508 (Fakharzadeh et al., 1991, *EMBO J.* 10:1565–1569)) and then rescreened with an hMDM2 cDNA clone containing nucleotides 40 to 702.

Twelve clones were obtained, and one of the clones was used to obtain thirteen additional clones by re-screening the same library. In total, twenty-five clones were obtained, partially or totally sequenced, and mapped. Sequence analysis of the twenty-five clones revealed several cDNA forms indicative of alternative splicing. The sequence shown in FIG. 1 is representative of the most abundant class and was assembled from three clones: c14-2 (nucleotides 1-949), c89 (nucleotides 467-1737), and c33 (nucleotides 390-2372). The 3' end of the untranslated region has not yet been cloned in mouse or human. The 5' end is likely to be at or near nucleotide 1. There was an open reading frame extending from the 5' end of the human cDNA sequence to nucleotide 1784. Although the signal for translation initiation could not be unambiguously defined, the ATG at nucleotide 312 was considered the most likely position for several reasons. First, the sequence similarity between hMDM2 and mMDM2 fell off dramatically upstream of nucleotide 312. This lack of conservation in an otherwise highly conserved protein suggested that the sequences upstream of the divergence may not code for protein. Second, an anchored polymerase chain reaction (PER) approach was employed in an effort to acquire additional upstream cDNA sequence. Ochman et al., 1985, In: *PCR Technology: Principles and Applications for DNA Amplification* (Erlich, ed.) pp. 105–111 (Stockton, N.Y.). The 5' ends of the PCR derived clones were very similar (within 3 bp) to the 5' ends of clones obtained from the cDNA library, suggesting that the 5' end of the hMDM2 sequence shown in FIG. 1 may represent the 5' end of the transcript. Third, in vitro translation of the sequence shown in FIG. 1, beginning with the methionine encoded by the nucleotide 3 12 ATG, generated a protein similar in size to that observed in human cells.

In FIG. 1, hMDM2 cDNA sequence, hMDM2 and mMDM2 nucleotide and amino acid sequences are compared. The mouse sequence is only shown where it differs from the corresponding human sequence. Asterisks mark the 5' and 3' boundaries of the previously published mMDM2 cDNA. Fakharzadeh et al., 1991, *EMBO J.* 10:1565–1569. Dashes indicate insertions. The mouse and human amino acid sequences are compared from the putative translation start site at nucleotide 3 12 through the conserved stop codon at nucleotide 1784.

Comparison of the human and mouse MDM2 coding regions revealed significant conservation at the nucleotide (80.3%) and amino acid (80.4%) levels. Although hMDM2 and mMDM2 bore little similarity to other genes recorded in current databases, the two promins shared several motifs. These included a basic nuclear localization signal (Tanaka, 1990, *FEBS Letters* 271:41–46) at codons 181 to 185, several casein kinase II serine phosphorylation sites (Pinna, 1990, *Biochem. et. Biophys. Acta.* 1054:267–284) at codons 166 to 169, 192 to 195, 269 to 272, and 290 to 293, an acidic activation domain (Ptashne, 1988, *Nature* 355:683–689) at codons 223 to 274, and two metal binding sites (Harrison, 1991, *Nature* 353:715) at codons 305 to 322 and 461 to 478, neither of which is highly related to known DNA binding domains. The protein kinase A domain noted in mMDM2 (Fakharzadeh et al., 1991, *EMBO J.* 10:1565–1569) was not conserved in hMDM2.

Example 2

To determine whether the hMDM2 protein could bind to human p53 protein in vitro, an hMDM2 expression vector was constructed from the cDNA clones. The hMDM2 expression vector was constructed in pBluescript SK+ (Stratagene) from overlapping cDNA clones. The construct contained the sequence shown in FIG. 1 from nucleotide 312 to 2176. A 42 bp black bettle virus ribosome entry sequence (Dasmahapatra et al., 1987, *Nucleic Acid Research* 15:3933) was placed immediately upstream of this hMDM2 sequence in order to obtain a high level of expression. This construct, as well as p53 (El-Deriy et al., 1992, *Nature Genetics*, in press) and MCC (Kinzler et al., 1991, *Science* 251:1366–1370) constructs in pBluescript SK+, were transcribed with T7 RNA polymerase and translated in a rabbit reticulocyte lysate (Promega) according to the manufacturer's instructions.

Although the predicted size of the protein generated from the construct was only 55.2 kd (extending from the methionine at nucleotide 312 to nucleotide 1784), in vitro translated protein migrated at approximately 95 kilodaltons.

Ten µl of lysate containing the three proteins (hMDM2, p53 and MCC), alone or mixed in pairs, were incubated at 37° C. for 15 minutes. One microgram (10 µl) of p53 Ab1 (monoclonal antibody specific for the C-terminus of p53) or Ab2 (monoclonal antibody specific for the N-terminus of p53) (Oncogene Science), or 5 µl of rabbit serum containing MDM2 Ab (polyclonal rabbit anti-hMDM2 antibodies) or preimmune rabbit serum (obtained from the rabbit which produced the hMDM2 Ab), were added as indicated. The polyclonal rabbit antibodies were raised against an *E. coli*-produced hMDM2-glutathione S-transferase fusion protein containing nucleotides 390 to 816 of the hMDM2 cDNA. Ninety µl of RIPA buffer (10 mM tris [pH 7.5], 1% sodium deoxycholate, 1% NP40, 150 mM NaCl, 0.1% SDS), SNNTE buffer, or Binding Buffer (El-Deriy et al., 1992, *Nature Genetics*, in press) were then added and the mixtures allowed to incubate at 4° C. for 2 hours.

Two milligrams of protein A sepharose were added to each tube, and the tubes were rotated end-over-end at 4° C. for 1 hour. After pelleting and washing, the immunoprecipitates were subjected to SDS-polyacrylamide gel electrophoresis and the dried gels autoradiographed for 10 to 60 minutes in the presence of Enhance (New England Nuclear).

FIG. 2 shows the co-precipitation of hMDM2 and p53. The three buffers produced similar results, although the co-precipitation was less efficient in SNNTE buffer containing 0.5M NaCl (FIG. 2, lanes 5 and 8) than in Binding Buffer containing 0.1M NaCl (FIG. 2 lanes 6 and 9).

In vitro translated hMDM2, p53 and MCC proteins were mixed as indicated above and incubated with p53 Ab1, p53 Ab2, hMDM2 Ab, or preimmune serum. Lanes 1, 4, 7, 10 and 14 contain aliquots of the protein mixtures used for immunoprecipitation. The bands running slightly faster than p53 are polypeptides produced from internal translation initiation sites.

The hMDM2 protein was not immunoprecipitated with monoclonal antibodies to either the C-terminal or N-terminal regions of p53 (FIG. 2, lanes 2 and 3). However, when in vitro translated human p53 was mixed with the hMDM2 translation product, the anti-p53 antibodies precipitated hMDM2 protein along with p53, demonstrating an association in vitro (FIG. 2, lanes 5 and 6). As a control, a protein of similar electrophoretic mobility from another gene (MCC (Kinzler et al., 1991, *Science* 251:1366–1370)) was mixed with p53. No co-precipitation of the MCC protein was observed (FIG. 2, lanes 8 and 9). When an in vitro translated mutant form of p53 ($175^{his}$) was mixed with hMDM2 protein, a similar co-precipitation of hMDM2 and p53 proteins was also observed.

Figure 5B:
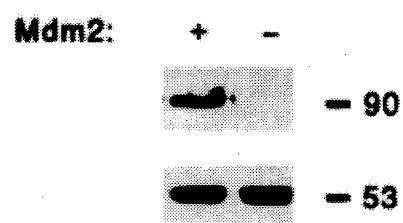
FIG. 5 shows the inhibition of p53-mediated transactivation by MDM2. Yeast were stably transfected with expression plasmids encoding p53, lex-VP16, MDM2 or the appropriate vector-only controls, as indicated. p53-responsive (bars a–c) or lexA-responsive (bars d–f) β-galactosidase reporter plasmids were used to assess the response. Inset: Western blot analysis demonstrating MDM2 (90 kD) and p53 (53 kD) expression in representative yeast strains. The strain indicated by a plus was transfected with expression vector encoding full length MDM2 and p53, while the strain indicated by a minus was transfected only with the p53 expression vector.

In the converse of the experiments described above, the anti-hMDM2 antibodies immunoprecipitated p53 when mixed with hMDM2 protein (FIG. 2, lane 15) but failed to precipitate p53 alone (FIG. 5, lane 13). Preimmune rabbit serum failed to precipitate either hMDM2 or p53 (FIG. 2, lane 16).

Example 3

In order to ascertain the chromosomal localization of hMDM2, somatic cell hybrids were screened with an hMDM2 cDNA probe. A human-hamster hybrid containing only human chromosome 12 was found to hybridize to the probe. Screening of hybrids containing portions of chromosome 12 (Turc-Carel et al., 1986, *Cancer Genet. Cytogenet.* 23:291–299) with the same probe narrowed the localization to chromosome 12q12-14.

Example 4

Previous studies have shown that this region of chromosome 12 is often aberrant in human sarcomas. Mandahl et al., 1987, Genes Chromosomes & Cancer 1:9–14; Turc-Carel et al., 1986, *Cancer Genet. Cytogenet.* 23:291–299; Meltzer et al., 199 1, *Cell Growth & Differentiation* 2:495–501. To evaluate the possibility that hMDM2 was genetically altered in such cancers, Southern blot analysis was performed.

FIG. 3 shows examples of the amplification of the hMDM2 gene in sarcomas. Cellular DNA (5 µg) was digested with EcoRI, separated by agarose gel electrophoresis, and transferred to nylon as described by Reed and Mann (*Nucl. Acids Res.*, 1985, 13:7207–7215). The cellular DNA was derived from five primary sarcomas (lanes 1–4, 6) and one sarcoma cell line (OsA-C1, lane 5). The filters were then hybridized with an hMDM2 cDNA fragment probe nucleotide 1-949 (see FIG. 1), or to a control probe which identifies fragments of similar size (DCC gene, 1.65 cDNA fragment). Fearon, 1989, *Science* 247:49–56. Hybridization was performed as described by Vogelstein et al. (*Cancer Research,* 1987, 47:4806–4813). A striking amplification of hMDM2 sequences was observed in several of these tumors. (See FIG. 3, lanes 2, 3 and 5). Of 47 sarcomas analyzed, 17 exhibited hMDM2 amplification ranging from 5 to 50 fold. These tumors included 7 to 13 liposarcomas, 7 of 22 malignant fibrous histiocytomas (MFH), 3 of 11 osteosarcomas, and 0 and 1 rhabdomyosarcomas. Five benign soft tissue tumors (lipomas) and twenty-seven carcinomas (colorectal or gastric) were also tested by Southern blot analysis and no amplification was observed.

Example 5

This example illustrates that gene amplification is associated with increased expression.

FIG. 4A illustrates hMDM2 expression as demonstrated by Northern blot analysis. Because of RNA degradation in the primary sarcomas, only the cell lines could be productively analyzed by Northern blot. RNA was separated by electrophoresis in a MOPS-formaldehyde gel and electrophoretically transferred to nylon filters. Transfer and hybridization were performed as described by Kinzler et al. (*Nature* 332:371–374, 1988). The RNA was hybridized to the hMDM2 fragment described in FIG. 3. Ten μg of total RNA derived, respectively, from two sarcoma cell lines (OsA-CL, lane 1 and RC13, lane 2) and the colorectal cancer cell line (CaCo-2) used to make the cDNA library (lane 3). Lane 4 contains 10 μg of polyadenylated CaCo-2 RNA. RNA sizes are shown in kb. In the one available sarcoma cell line with hMDM2 amplification, a single transcript of approximately 5.5 kb was observed (FIG. 4A, lane 1). The amount Of this transcript was much higher than in a sarcoma cell line without amplification (FIG. 4A, lane 2) or in a carcinoma cell line (FIG. 4A, lane 3). When purified mRNA (rather than total RNA) from the carcinoma cell line was used for analysis, an hMDM2 transcript of 5.5 kb could also be observed (FIG. 4A, lane 4).

Figure 4B:
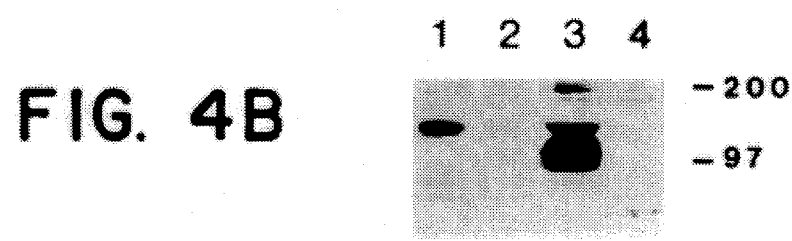

FIG. 4B illustrates hMDM2 expression as demonstrated by Western blot analysis of the sarcoma cell lines RC13 (lane 1), OsA-CL (lane 3), HOS (lane 4), and the carcinoma cell line CaCo-2 (lane 2).

Figure 4C:

FIG. 4C illustrates hMDM2 expression as demonstrated by Western blot analysis of primary sarcomas. Lanes 1 to 3 contain protein from sarcomas with hMDM2 amplifications, and lanes 4 and 5 contain protein from sarcomas without hMDM2 amplification.

Western blots using affinity purified MDM2 Ab were performed with 50 μg protein per lane as described by Kinzler et al. (*Mol. Cell. Biol.*, 1990, 10:634–642), except that the membranes were blocked in 10% nonfat dried milk and 10% goat serum, and secondary antibodies were coupled to horseradish peroxidase, permitting chemiluminescent detection (Amersham ECL). MDM2 Ab was affinity purified with a pATH-hMDM2 fusion protein using methods described in Kinzler et al. (*Mol. Cell. Biol.* 10:634–642, 1990). Non-specifically reactive proteins of about 75–85, 105–120 and 170–200 kd were observed in all lanes, irrespective of hMDM2 amplification status. hMDM2 proteins, of about 90–97 kd, were observed only in the hMDM2-amplified tumors. Protein marker sizes are shown in kd.

A protein of approximately 97 kilodaltons was expressed at high levels in the sarcoma cell line with hMDM2 amplification (FIG. 4B, lane 3), whereas no expression was evident in two sarcoma cell lines without amplification or in the carcinoma cell line (FIG. 4B, lanes 1, 2 and 4). Five primary sarcomas were also examined by Western blot analysis. Three primary sarcomas with amplification expressed the same size protein as that observed in the sarcoma cell line (FIG. 4C, lanes 1–3), while no protein was observed in the two sarcomas without amplification (FIG. 4C, lanes 4 and 5).

Expression of the hMDM2 RNA in the sarcoma with amplification was estimated to be at least 30 fold higher than that in the other lines examined. This was consistent with the results of Western blot analysis.

The above examples demonstrate that hMDM2 binds to p53 in vitro and is genetically altered (i.e., amplified) in a significant fraction of sarcomas, including MFH, liposarcomas, and osteosarcomas. These are the most common sarcomas of soft tissue and bone. Weiss and Enzinger, 1978, *Cancer* 41:2250–2266; Malawer et al., 1985, In: *Cancer: Principles and Practice of Oncology,* DeVita et al., Eds., pp. 1293–1342 (Lippincott, Philadelphia).

Human MDM2 amplification is useful for understanding the pathogenesis of these often lethal cancers.

MDM2 may functionally inactivate p53 in ways similar to those employed by virally encoded oncoproteins such as SV40 T-antigen, adenovirus E1B, and HPV E6. Lane and Bechimol, 1990, *Genes and Development* 4: 1–8; Werness et al., 1990, *Science* 248:76. Consistent with this hypothesis, no sarcomas with hMDM2 amplification had any of the p53 gene mutations that occur commonly in other tumors. hMDM2 amplification provides a parallel between viral carcinogenesis and the naturally occurring genetic alterations underlying sporadic human cancer. The finding that expression of hMDM2 is correspondingly elevated in tumors with amplification of the gene are consistent with the finding that MDM2 binds to p53, and with the hypothesis that overexpression of MDM2 in sarcomas allows escape from p53 regulated growth control. This mechanism of tumorigenesis has striking parallels to that previously observed for virally induced tumors (Lane and Bechimol, 1990, Genes and Development 4:1–8; Werness et al., 1990, *Science* 248:76), in which viral oncogene products bind to and functionally inactivate p53.

Example 6

This example demonstrates that MDM2 expression inhibits p53-mediated transactivation.

To determine if MDM2 could influence the ability of p53 to activate transcription, expression vectors coding for the two proteins were stably transfected into yeast along with a p53-responsive reporter construct. The reporter consisted of a β-galactosidase gene under the transcriptional control of a minimal promoter and a multimerized human DNA sequence which strongly bound p53 in vitro (Kern, S. E., et al., *Science* 256:827–830 (1992). Reporter expression was completely dependent on p53 in this assay (FIG. 5, compare bars a and c). MDM2 expression was found to inhibit p53-mediated transactivation of this reporter 16-fold relative to isogeneic yeast lacking MDM2 expression (FIG. 5, compare bars a and b). Western blot analysis confirmed that p53 (53 kD) was expressed equivalently in strains with and without MDM2 (90 kD) (FIG. 1, inset).

METHODS. The MDM2 expression plasmid, pPGK-MDM2, was constructed by inserting the full length MDM2 cDNA (Oliner, J. D., et al., *Nature* 358:80–83 (1992)) into pPGK (Poon, D. et al., *Mol. and Cell. Biol.* 1111:4809–4821 (1991)), immediately downstream of the phosphoglycerate kinase constitutive promoter. Galactose-inducible p53 (pRS314SN, Nigro, J. M., et al., *Mol. and Cell. Biol.* 12:1357–1365 (1992)), lexA-VP16 (YVLexA, Dalton, S., et al., *Cell* 68:597–612 (1992)), and lexA (YLexA, YVLexA minus VP16) plasmids were used as indicated. The reporters were PG16-lacZ (Kern, S. E. et al., *Science* 256:827–830 (1992)) (p53-responsive) and pJK103 (Kamens, J., et al., *Mol. Cell. Biol.* 10:2840–2847 (1990)) (lexA-responsive). *S. cerevisiae* strain pEGY48 was transformed as described (Kinzler, K. W. et al., *Nucl. Acids Res.* 17:3645–3653 (1989)). Yeast strains represented by bars a-c were grown at 30° C. to mid-log phase in selective liquid medium containing 2 % raffinose as the carbon source, induced for 30 minutes by the addition of 2% galactose, harvested, and lysed as described (Kern, S. E. et al., *Science* 256:827–830 (1992)). The strains represented by bars d-f were treated similarly, except that the cells were induced in galactose for 4 hours to obtain measurable levels of β-galactosidase. β-galactosidase activities shown represent the mean of three to five experimental values (error bars indicate s.e.m.). Protein concentrations were determined by a Coomassie blue-based (bio-Rad) assay. The β-galactosidase assays were performed with AMPGD chemiluminescent substrate and Emerald enhancer (Tropix) according to the manufacturer's instructions. β-galactosidase activities of bars b and c are shown relative to that of bar A; β-galactosidase activities of bars e and f are shown relative to that of bar d. Western blots were performed as described (Oilher, J. D., et al., *Nature* 358:80–83 (1992)), using p53 Ab1801 (lower panel, Oncogene Science) or MDM2 polyclonal antibodies (Oliner, J. D., et al., *Nature* 358:80–83 (1992)) (upper panel).

To ensure that this inhibition was not simply a general transcriptional down regulation mediated by the expression of the foreign MDM2 gene, a yeast strain was created that contained a different transcriptional activator (lexA-VP16, consisting of the lexA DNA binding domain fused to the VP16 acidic activation domain), a similar reporter (with a lexA-responsive site upstream of β-galactosidase gene), and the same MDM2 expression vector. The results shown in FIG. 1 (bars d & e) demonstrate that lexA-VP16 transactivation was unaffected by the presence of MDM2. Furthermore, MDM2 expression had no apparent effect on the growth rate of the cells.

Example 7

This example demonstrates the domains of p53 and MDM2 which interact with each other.

To gain insight into the mechanism of the MDM2-mediated p53 inhibition, the domains of MDM2 and p53 responsible for binding to one another were mapped. The yeast system used to detect protein-protein binding takes advantage of the modular nature of transcription factor domains (Keegan, L., et al., *Science* 231:699–704 (1986); Chien, C.-T., *Proc. Natl. Acad. Sci. U.S.A.* 88:9578–9582 (1991); Brent, R., et al., *Cell* 43:729–731 (1985); Ma, J., et al., *Cell* 55:4430446 (1988). Generically, if protein 1 (fused to a sequence-specific DNA binding domain) is capable of binding to protein 2 (fused to a transcriptional activation domain), then co-expression of both fusion proteins will result in transcriptional activation of a suitable reporter. In our experiments, the lexA DNA binding domain (amino acids 2-202) and the B42 acidic activation domain (AAD) were used in the fusion constructs. The reporter (Kamens, J., et al., *Mol. Cell. Biol.* 10:2840–2847 (1990); contained a lexA-responsive site upstream of a β-galactosidase gene. As an initial control experiment, full length MDM2 was inserted into the lexA fusion vector, and full length p53, supplying its intrinsic activation domain was inserted into a non-fusion vector. The combination resulted in the activation of the lexA-responsive reporter, while the same expression constructs lacking either the MDM2 or p53 cDNA inserts failed to activate β-galaetosidase (Table I, strains 1, 2, and 3). Thus, activation was dependent upon MDM2-p53 binding.

This assay was then applied to mapping the interaction domains of each protein. Full length cDNA fragments encoding MDM2 or p53 were randomly sheared by sonication, amplified by polymerase chain reaction, size fractionated, cloned into the appropriate fusion vectors and transfected into yeast along with the reporter and the full length version of the other protein.

METHODS. Full length MDM2 cDNA in pBluescript SK +(Stratagene) was digested with XhoI and BamHI to excise the entire insert. After agarose gel purification, the insert was sheared into random fragments by sonication, polished with the Klenow fragment of DNA polymerase I, ligated to catch linkers, and amplified by the polymerase chain reaction as described (Kinzler, K. W., et al., *Nucl. Acids Res.* 17:3645–3653 (1989)). The fragments were fractionated on an acrylamide gel into size ranges of 100–400 bp or 400–1000 pb, cloned into lexA(1-202)+PL (Ruden, D. M., et al., *Nature* 350:250–252 (1991)), and transfected into bacteria (XL-1 Blue, Stratagene). At least 10,000 bacterial colonies were scraped off agar plates, and the plasmid DNA was transfected into a strain of pEGY48 containing pRS3 14N (p53 expression vector) and pIK103 (lexA-responsive β-galactosidase reporter). Approximately 5,000 yeast clones were plated on selective medium containing 2 % dextrose, and were replica-plated onto glalctose- and X-gal-containing selective medium. Blue colonies (17) appeared only on the plates containing the larger fragments of MDM2. The 17 isolated colonies were tested for blue color in this assay both in the presence and in the absence of galactose (p53 induction); all tested positive in the presence of galactose but only 2 of the 17 tested positive in its absence. MDM2-containing plasmid DNA extracted from the 17 yeast clones was selectively transferred to bacterial strain KC8 and sequenced from the lexA-MDM2 junction. The MDM2 sequences of the two p53-independent clones are diagrammed in FIG. 6A. The MDM2 sequences of the remaining 15 p53-dependent clones coded for peptides ranging from 135 to 265 a.a. in length and began exclusively at the initiator methionine. Three of the MDM2 sequences obtained are shown at the top of FIG. 6B. The lower 6 sequences were genetically engineered (using the polymerase chain reaction and appropriate primers) into lexA(1-202)+PL and subsequently tested to further narrow the binding region.

Fragments of p53 were also cloned into pJG4-5, producing a fusion protein C-terminal to the 1342 acidic activation domain and incorporating an epitope of hemagglutinin. The clones were transfected into a strain of pEGY48 already containing lex-MDM2 (plex-202+PL containing full length MDM2) and pJK103. The top three p53 sequences shown in FIG. 6C. were derived from yeast obtained by colony screening, whereas the lower three were genetically engineered to contain the indicated fragments.

The resultant yeast colonies were examined for β-galactosidase activity in situ. Of approximately 5000 clones containing MDM2 fragments fused to the lexA DNA binding domain, 17 were found to score positively in this assay. The clones could be placed into two classes. The first class (two clones) expressed low levels of β-galactosidase (about 5-fold less than the other fifteen clones) and β-galactosidase expression was independent of p53 expression (FIG. 6A). These two clones encoded MDM2 amino acids 190-340 and 269-379, respectively. The region shared between these two clones overlapped the only acidic domain in MDM2 (amino acids 230-301). This domain consisted of 37.5 % aspattic and glutamic acid residues but no basic amino acids. This acidic domain appears to activate transcription only when isolated from the rest of the MDM2 sequence, because the entire MDM2 protein fused to lexA had no measurable β-galactosidase activity in the same assay (Table I, strain 3). The other class (15 clones) each contained the amino terminal region of MDM2 (FIG. 6B). The β-galactosidase activity of these clones was dependent on p53 co-expression. To narrow down the region of interaction, we generated six additional clones by genetic engineering. The smallest tested region of MDM2 which could functionally interact with full length p53 contained MDM2 codons 1 to 118 (FIG. 6B). The relatively large size of the domain required for interaction was consistent with the fact that when small sonicated fragments of MDM2 were used in the screening assay (200 bp instead of 600 bp average size), no positively scoring clones were obtained.

In a converse set of experiments, yeast clones containing fragments of p53 fused to the B42 AAD were screened for lexA-responsive reporter expression in the presence of a lexA-MDM2 fusion protein. Sequencing of the 14 clones obtained in the screen revealed that they could be divided into three subsets, one containing amino acids 1-41, a second containing amino acids 13-57, and a third containing amino acids 1-50 (FIG. 6C). The minimal overlap between these three fragments contained codons 13-41. Although this minimal domain was apparently necessary for interaction with MDM2, it was insufficient, as the fragments required 9-12 amino acids on either side of codons 13-41 for activity (FIG. 6C). To further test the idea that the amino terminal region of p53 was required for MDM2 binding, we generated an additional yeast strain expressing the lexA-DNA binding domain fused to p53 codons 74-393) and the B42 acidic activation domain fused to full length MDM2. These strains failed to activate the same lexA-responsive reporter (Table I, strain 8), as expected if the N-terminus of p53 were required for the interaction.

TABLE I

| STRAIN NUMBER | p53 CONSTRUCT | MDM2 CONSTRUCT | ACTIVATION |
|---|---|---|---|
| 1 | p53[a] | Vector[b] | − |
| 2 | p53[a] | lexA-MDM2[b] | + |
| 3 | Vector[a] | lexA-MDM2[b] | − |
| 4 | p53[a] | lexA-MDM2 (1–118)[b] | + |
| 5 | Vector[a] | lexA-MDM2 (1–118)[b] | − |
| 6 | B42-p53 (1–41)[c] | lexA-MDM2[b] | + |
| 7 | B42-p53 (1–41)[c] | Vector[b] | − |
| 8 | lexA-p53 (74–393)[b] | B42-MDM2[c] | − |
| 9 | p53 (1–137)[a] | lexA-MDM2[b] | − |

The MDM2 and p53 proteins expressed in each strain, along with the relevant reporters, are indicated. Numbers in parentheses refer to the MDM2 or p53 amino acids encoded (absence of parentheses indicated full length protein, that is, MDM2 amino acids 1 to 491 or p53 amino acids 1 to 393). The lexA-responsive β-galactosidase reporter plasmid (pJK103, Kamens, J., et al., Mol. Cell. Biol. 10:2840–2847 (1990)) was present in all strains.
[a]pRS314 vector (Nigro, J. M., et al., Mol. and Cell. Biol. 12:1357–1365 (1992).
[b]plex(1–202) +PL vector, containing lexA DNA binding domain fused to insert (Ruden, D. M., et al., Nature 350:250–252 (1991).
[c]JG4-5 vector, containing B42 activation domain fused to insert.
[d](+) indicates that colonies turned blue following 24 hours of incubation on X-gal-containing selective medium, while (−) indicates that colonies remained white following 72 hours of incubation.

Figure 6:
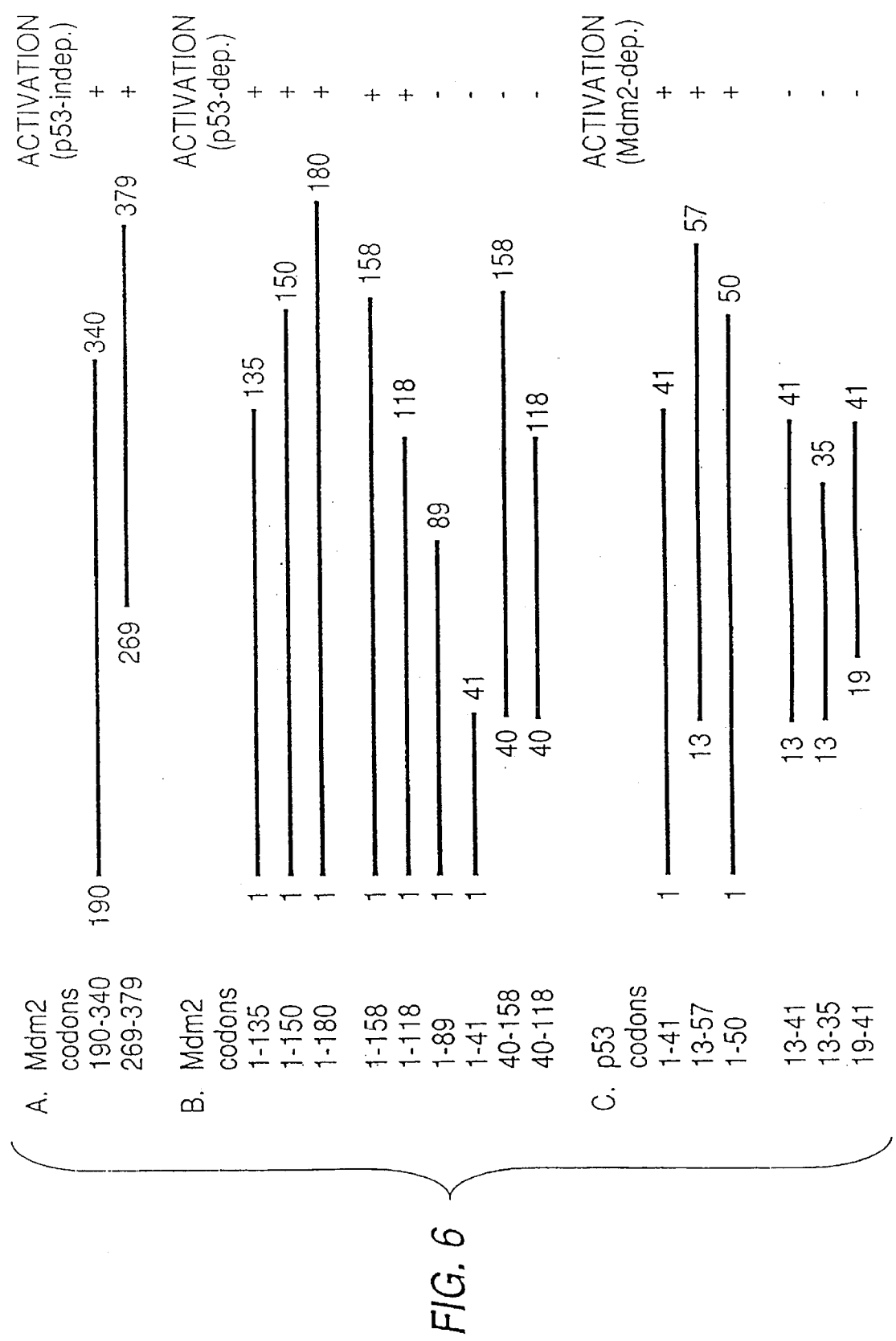
FIG. 6 shows the determination of MDM2 and p53 domains of interaction.
Figure 7A:
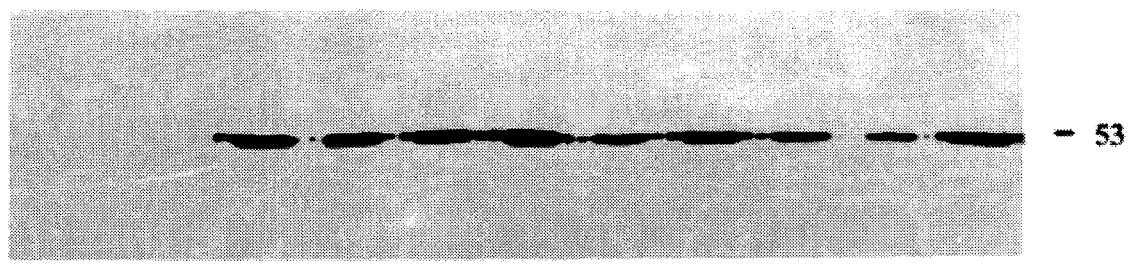
FIG. 7A. Protein expression using the MDM2 codons shown at the top contained in a fusion vector. Upper panel probed with p53 Ab2 detecting p53; lower panel probed with anti-lexA polyclonal antibodies (lex Ab) detecting MDM2 fusion proteins of 30–50 kD.
Figure 7B:
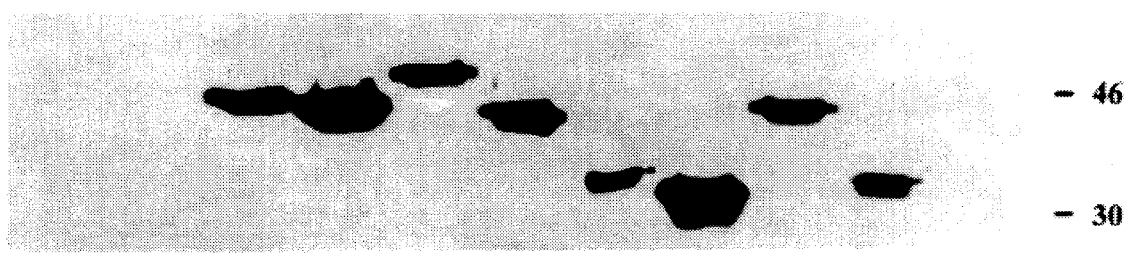
FIG. 7B. Protein expression using the p53 codons shown at the top contained in a fusion vector. Upper panel probed with Lex Ab detecting the lexA-full length MDM2 fusion protein of 112 kD; lower panel probed with HA Ab (a monoclonal antibody directed against the hemagglutinin epitope tag, Berkeley Antibody) detecting p53 fusion proteins of approximately 25–30 kD.
Figure 7C:
FIG. 7 shows protein expression from the yeast strains described in FIG. 6. Western blot analysis was performed as described (Oliner, J. D., et al., Nature 358:80–83 (1992)), using 20 μg of protein per lane.
Figure 7D:
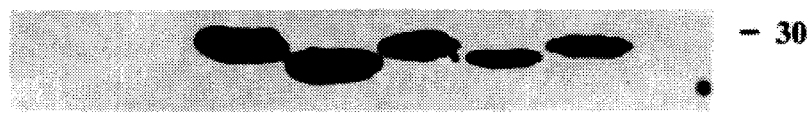

Sequence analysis showed that all p53 and MDM2 fragments noted in FIG. 6 were ligated in frame and in the correct orientation relative to the B42 and lexA domains, respectively. Additionally, all clones compared in FIG. 6 expressed the relevant proteins at similar levels, as shown by Western blotting (FIG. 7).

Figure 8B:
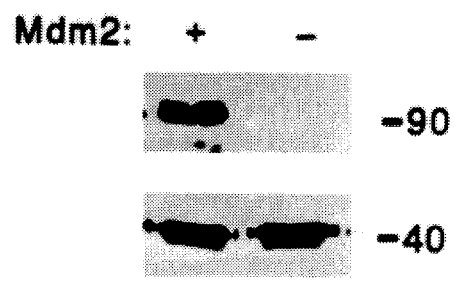
FIG. 8 shows the inhibition of the p53 activation domain by MDM2. Yeast were transfected with expression vectors encoding a lexA-p53 (p53 codons 1–73) fusion (bars a and b) or lexA alone (bar c). Strain b also expressed full length MDM2, and all strains contained the lexA-responsive β-galactosidase reporter plasmid. Inset: Upper panel probed with MDM2 polyclonal antibodies detecting full length MDM2 (90 kD); lower panel probed with lex Ab detecting the lex-p53 fusion protein of 40 kD.

The most striking results of these mapping experiments was that the region of p53 required to bind MDM2 was almost identical to the previously identified acidic activation domain of p53 (amino acids 20-42) (Unger, T., et al., EMBO J. 11:1383–1390 (1992); Miller, C. W., et al., Proc. Am. Assoc. Cancer Res. 33:386 (1992). This suggested that MDM2 inhibits p53-mediated transcriptional activation by "concealing" the activation domain of p53 from the transcriptional machinery. If this were true, the p53 activation domain, in isolation from the rest of the p53 protein, should still be inhibitable by full length MDM2. To test this hypothesis, we produced a hybrid protein containing the p53 activation domain (codons 1-73) fused to the lexA-DNA binding domain. This construct exhibited strong transcriptional activation of a lexA-responsive reporter (FIG. 8), as predicted from previous experiments in which the p53 activation domain was fused to another DNA binding domain (Fields, S., et al., Science 249:1046–1049 (1990); Raycroft, L., et al., Science 249:1049–1051 (1990)). The lexA-p53 DNA construct was stably expressed in yeast along with the full length MDM2 expression vector (or the vector alone). MDM2 expression resulted in a five-fold decrease in reporter activity, demonstrating that MDM2 can specifically inhibit the function of the p53 activation domain regardless of the adjacent protein sequences tethering p53 to DNA (FIG. 8).

METHODS. Strains were grown to mid-log phase in 2 % dextrose before induction of p53 expression for 2 hours by the addition of 2 % galactose. The lex-p53 construct was identical to lex-VP16 (YVlexA, Dalton, S., et al., Cell 68:597–612 (1992)) except that VP16 sequences were replaced by p53 sequences encoding amino acids 1 to 73.

The results obtained in the experiments discussed herein raise an interesting paradox. If MDM2 binds to (FIG. 6) and conceals (FIG. 8) the p53 activation domain from the transcriptional machinery, how could the lexA-MDM2-p53 complex activate transcription from the lexA-responsive reporter Table I, strain 2)? Because the only functional activation domain in the lexA-MDM2-p53 complex of strain 2 is expected to be contributed by p53, one might predict that it would be concealed by binding to MDM2 and thereby fail to activate. A potential resolution of this paradox is afforded by knowledge that p53 exists as a homotetramer (Stenger, J. E., et al., Mol. Carcinogenesis 5:102–106 (1992); Sturzbecher, H. W. et al., Oncogene 7:1513–1523 (1992). Thus the activation noted in the lexA-MDM2-p53 complex could be due to the presence of four individual activation domains contributed by the p53 tetramer, not all of which were concealed by MDM2. As a direct test of this issue, the domain of p53 required for homo-oligomerization (Stenger, J. E., et al., Mol. Carcinogenesis 5:102–106 (1992); Sturzbecher, H. W. et al., Oncogene 7:1513–1523 (1992) (the C-terminus) was removed from the p53 expression construct, so that it consisted of only codons 1-137. This truncated p53 polypeptide retained the entire activation domain (as shown in FIG. 8, bar a) and the entire domain required for interaction with MDM2 (Table I, strain 6). Yet, when allowed to interact with lexA-MDM2, no transactivation of the lexA-responsive reporter was observed (Table I, strain 9). Because p53 did not inhibit lexA-MDM2 binding to the lexA reporter (Table I, strain 2), the result of strain 9 is likely to be due to a direct inhibition of the isolated p53 activation domain by MDM2.

Example 8

This example illustrates the production and characterization of antibodies specific for MDM2 epitopes.

The antigen preparations used to intraperitoneally immunize female (BALB/c X C57BL/6)F1 mice comprised bacterially expressed, glutathione-column purified glutathione-S-transferase-MDM2 (GST-MDM2) fusion protein. (One preparation was further purified on a polyacrylamide gel and electroeluted.) The fusion protein contains a 16 kD amino terminal potion of human MDM2 protein (amino acids 27 to 168). For immunization, the fusion protein was mixed with Ribi adjuvant (Ribi Immunochem Research, Inc.).

Two mice were sacrificed and their spleen cells fused to SP2/0s myeloma cells (McKenzie, et al., Oncogene, 4:543–548, 1989). Resulting hybridomas were screened by ELISA on trpE-MDM2 fusion protein-coated microtiter wells. The trpE-MDM2 fusion protein contains the same portion of MDM2 as the GST-MDM2 fusion protein. Antigen was coated at a concentration of 1 µg/ml.

A second fusion was performed as described except hybridomas were screened on electroeluted, glutathione purified GST-MDM2. Positive hybridomas from both fusions were expanded and single cell subcloned. Subclones were tested by Western Blot for specificity to the 55 kD trpE-MDM2 and the 43 kD GST-MDM2 fusion proteins.

Two Western Blot positive subclones (1F2 and JG3) were put into mice for ascites generation. The resulting ascites were protein A purified. Both purified monoclonal antibodies tested positive by Western Blot and immunoprecipitation for the 90 kD migrating MDM2 protein present in a human osteosarcoma cell line (OsA-CL), which overexpresses MDM2, and negative in the HOS osteosarcoma, which does not overexpress MDM2.

ED9 was protein G-purified from ascites and found to be specific in cryostat immunohistochemistry for MDM2 in osteosarcoma cells, as was IF2.

Example 9

This example demonstrates the expression and detection of MDM2 at the cellular level.

To evaluate MDM2 expression at the cellular level, we produced monoclonal antibodies against bacterially generated fusion proteins containing residues 27 to 168 of MDM2. (See example 8.) Of several antibodies tested, mAb IF-2 was the most useful, as it detected MDM2 in several assays. For initial testing, we compared proteins derived from OsA-CL, a sarcoma cell line with MDM2 amplification but without p53 mutation (Table II) and proteins from SW480, a colorectal cancer cell line with p53 mutation (Barak et al., *EMBO* 12:461–468 (1993)) but without MDM2 amplification (data not shown). The mAb IF-2 detected an intense 90 kd band plus several other bands of lower molecular weight in OsA-CL extracts, and a much less intense 90 kd band in SW480 extracts. We could not distinguish whether the low molecular weight bands in OsA-CL were due to protein degradation or alternative processing of MDM2 transcripts. The more than 20-fold difference in intensity between the signals observed in OsA-CL and SW480 is consistent with the greater than 20-fold difference in MDM2 gene copy number in these two lines. Conversely, the 53 kd signal detected with p53-specific mAb 1801 was much stronger in SW480 than in OsA-CL consistent with the presence of a mutated p53 in SW480.

Cells grown on cover slips were then used to assess the cellular localization of the MDM2 protein. A strong signal, exclusively nuclear, was observed in OsA-CL cells with the IF-2 mAb and a weaker signal, again strictly nuclear, was observed in SW480. The nuclear localization of MDM2 is consistent with previous studies of mouse cells (Barak et al., *EMBO* 12:461–468 (1993)) and the fact that human MDM2 contains a nuclear localization signal at residues 179 to 186. Reactivity with the p53-specific antibody was also confined to the nuclei of these two cell lines, with the relative intensities consistent with the Western blot results.

The IF-2 mAb was then used (at 5 μg/ml) to stain the seven primary sarcomas noted above. The nuclei of two of them (tumors #3 and #10) stained strongly. Both of these tumors contained MDM2 gene amplification (Table II). In the five tumors without amplification, little or no MDM2 reactivity was observed.

TABLE II

| TUMOR # | TUMOR ID | TYPE[a] | MDM2 AMPLIFICATION[b] | P53 ALTERATION[c] | OVER-EXPRESSION[d] |
|---|---|---|---|---|---|
| 1 | M-2 | MFH | ABSENT | DELETION/REARRANGEMENT | NONE |
| 2 | M-5 | MFH | ABSENT | CGC-CUC MUTATION; Arg(158)-His | p53 |
| 3 | M-7 | MFH | PRESENT | NONE OBSERVED | MDM2 |
| 4 | M-8 | MFH | ABSENT | DELETION | NONE |
| 5 | M-14 | MFH | ABSENT | NONE OBSERVED | N.T. |
| 6 | M-15 | MFH | ABSENT | DELETION | N.T. |
| 7 | M-16 | MFH | ABSENT | NONE OBSERVED | NONE |
| 8 | M-17 | MFH | ABSENT | NONE OBSERVED | N.T. |
| 9 | M-18 | MFH | ABSENT | OVEREXPRESSED | p53 |
| 10 | M-20 | MFH | PRESENT | NONE OBSERVED | MDM2 |
| 11 | L-5 | LIPOSARCOMA | ABSENT | NONE OBSERVED | N.T. |
| 12 | L-7 | LIPOSARCOMA | ABSENT | AAC-AGC MUTATION; Asn(239)-Ser | N.T. |
| 13 | L-9 | LIPOSARCOMA | PRESENT | NONE OBSERVED | N.T. |
| 14 | L-11 | LIPOSARCOMA | ABSENT | NONE OBSERVED | N.T. |
| 15 | KL5B | LIPOSARCOMA | ABSENT | CAG-UAG MUTATION; Gln(144)-Stop | N.T. |
| 16 | KL7 | LIPOSARCOMA | PRESENT | NONE OBSERVED | N.T. |
| 17 | KL10 | LIPOSARCOMA | ABSENT | NONE OBSERVED | N.T. |
| 18 | KL11 | LIPOSARCOMA | ABSENT | GGT-GAT MUTATION; EXON 5 SPLICE DONOR SITE | N.T. |
| 19 | KL12 | LIPOSARCOMA | ABSENT | NONE OBSERVED | N.T. |
| 20 | KL28 | LIPOSARCOMA | PRESENT | NONE OBSERVED | N.T. |
| 21 | KL30 | LIPOSARCOMA | PRESENT | NONE OBSERVED | N.T. |
| 22 | S189 | LIPOSARCOMA | PRESENT | NONE OBSERVED | N.T. |
| 23 | S131B | LIPOSARCOMA | ABSENT | NONE OBSERVED | N.T. |
| 24 | OSA-CL | MFH | PRESENT | NONE OBSERVED | MDM2 |

[a]MFH = malignant fibrous histiocytoma
[b]as assessed by Southern blot
[c]as assessed by Southern blot, sequencing of exons 5–8, or immunohistochemical analysis
[d]as assessed by immunohistochemical analysis; N.T. = not tested

We claim:

1. An isolated antibody which specifically binds to human MDM2 protein as shown in SEQ ID NO:3.

2. The isolated antibody of claim 1 wherein the antibody binds only to proteins encoded by human MDM2 transcripts.

3. The isolated antibody of claim 1 wherein the antibody does not bind to human proteins of M, 75–85 kD, 105–120 kD, or 170–200 kD, as measured by non-denaturing SDS gel electrophoresis.

4. The isolated antibody of claim 1 wherein the antibody binds to the epitope bound by antibodies secreted by hybridoma IF2 (ATCC HB 11290).

5. The antibody of claim 1 wherein the antibody binds the to epitope bound by antibodies secreted by hybridoma ED9 (ATCC HB 11291).

6. The antibody of claim 1 wherein the antibody is monoclonal.

7. A kit for detecting elevated expression of a human MDM2 protein in a human tissue or body fluid sample comprising an isolated antibody which specifically binds to human MDM2 protein as shown in SEQ ID NO:3 and written instructions for determining elevated expression of human MDM2 protein.

8. The isolated antibody of claim 1 wherein the antibody binds only to epitopes encoded by human MDM2 transcripts.

9. The isolated antibody of claim 1 wherein the antibody does not bind to mouse MDM2 protein as shown in SEQ ID NO: 4.

10. The isolated antibody of claim 2 wherein the antibody does not bind to mouse MDM2 protein as shown in SEQ ID NO: 4.

11. The isolated antibody of claim 8 wherein the antibody does not bind to mouse MDM2 protein as shown in SEQ ID NO: 4.

12. A hybridoma cell line designated ED9 (ATCC HB 11291).

13. A hybridoma cell line designated IF2 (ATCC HB 11290).

14. An isolated antibody secreted by the hybridoma cell line of claim 12.

15. An isolated antibody secreted by the hybridoma cell line of claim 13.

* * * * *

UNITED STATES PATENT AND TRADEMARK OFFICE
CERTIFICATE OF CORRECTION

PATENT NO. : 5,618,921
DATED : April 8, 1997
INVENTOR(S) : Marilee Burrell, David E. Hill, Kenneth W. Kinzler and Bert Vogelstein It is certified that error appears in the above-indentified patent and that said Letters Patent is hereby corrected as shown below:

At column 3, lines 31-32, delete these lines in their entirety.

In the Claims

Claim 3, line 2, change "M," to --$M_r$--.

Signed and Sealed this

Second Day of September, 1997

*Attest:*

BRUCE LEHMAN

*Attesting Officer*  Commissioner of Patents and Trademarks